US009450290B2

(12) United States Patent
Koyama et al.

(10) Patent No.: US 9,450,290 B2
(45) Date of Patent: *Sep. 20, 2016

(54) HEALTH DATA COLLECTING SYSTEM AND SEMICONDUCTOR DEVICE

(71) Applicant: Semiconductor Energy Laboratory Co., Ltd., Atsugi-shi, Kanagawa-ken (JP)

(72) Inventors: Jun Koyama, Sagamihara (JP); Shunpei Yamazaki, Setagaya (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 297 days.

This patent is subject to a terminal disclaimer.

(21) Appl. No.: 13/965,327

(22) Filed: Aug. 13, 2013

(65) Prior Publication Data

US 2013/0328731 A1     Dec. 12, 2013

Related U.S. Application Data

(63) Continuation of application No. 12/796,064, filed on Jun. 8, 2010, now Pat. No. 8,547,221, which is a continuation of application No. 11/660,753, filed as application No. PCT/JP2005/016373 on Aug. 31, 2005, now Pat. No. 7,768,391.

(30) Foreign Application Priority Data

Sep. 3, 2004  (JP) ................. 2004-257646

(51) Int. Cl.
*H01Q 1/22*     (2006.01)
*A61B 5/00*     (2006.01)
(Continued)

(52) U.S. Cl.
CPC ........... *H01Q 1/2283* (2013.01); *A61B 5/0002* (2013.01); *G06K 19/0716* (2013.01);
(Continued)

(58) Field of Classification Search
CPC ............. H01Q 1/2208; H01Q 1/2216; H01Q 1/2225; H01Q 1/2283
USPC ........................................................ 343/718
See application file for complete search history.

(56) References Cited

U.S. PATENT DOCUMENTS

| 5,300,120 A | 4/1994 | Knapp et al. |
| 5,674,288 A | 10/1997 | Knapp et al. |

(Continued)

FOREIGN PATENT DOCUMENTS

| CN | 1193192 | 9/1998 |
| EP | 1 439 410 | 7/2004 |

(Continued)

OTHER PUBLICATIONS

International Search Report (Application No. PCT/JP2005/016373) dated Oct. 25, 2005.

(Continued)

*Primary Examiner* — Sue A Purvis
*Assistant Examiner* — Patrick Holecek
(74) *Attorney, Agent, or Firm* — Robinson Intellectual Property Law Office; Eric J. Robinson

(57) ABSTRACT

Conventionally, people have to go to the place where a measurement instrument for health data is, to obtain health data and the like. Further, even when using a portable measurement instrument, people have to manage data by themselves, thus health data cannot be managed rapidly. According to the invention, a modulating circuit, a demodulating circuit, a logic circuit, a sensor circuit, and an antenna circuit are provided over an insulating substrate, thereby data sensed by the sensor circuit is transmitted wirelessly. According to the invention, health data on the living body (for example a human body) is sensed and can be rapidly detected.

23 Claims, 18 Drawing Sheets

(51) Int. Cl.

| | | |
|---|---|---|
| *G06K 19/07* | (2006.01) | |
| *G06K 19/077* | (2006.01) | |
| *H01L 27/12* | (2006.01) | |
| *H01L 27/13* | (2006.01) | |
| *H01Q 1/27* | (2006.01) | |
| *H01Q 1/36* | (2006.01) | |
| *A61B 5/02* | (2006.01) | |

(52) U.S. Cl.
CPC ..... *G06K19/0775* (2013.01); *G06K 19/07745* (2013.01); *G06K 19/07749* (2013.01); *G06K 19/07779* (2013.01); *G06K 19/07783* (2013.01); *G06K 19/07786* (2013.01); *H01L 27/1214* (2013.01); *H01L 27/13* (2013.01); *H01Q 1/2225* (2013.01); *H01Q 1/273* (2013.01); *H01Q 1/362* (2013.01); *A61B 5/02* (2013.01); *H01L 2221/6835* (2013.01); *H01L 2924/0002* (2013.01)

(56) References Cited

U.S. PATENT DOCUMENTS

| | | |
|---|---|---|
| 5,716,407 A | 2/1998 | Knapp et al. |
| 5,725,578 A | 3/1998 | Knapp et al. |
| 5,833,603 A | 11/1998 | Kovacs et al. |
| 5,855,609 A | 1/1999 | Knapp |
| 5,977,431 A | 11/1999 | Knapp et al. |
| 6,130,613 A | 10/2000 | Eberhardt et al. |
| 6,291,877 B1 | 9/2001 | Usami et al. |
| 6,313,402 B1 | 11/2001 | Schreiber et al. |
| 6,380,560 B1 | 4/2002 | Yamazaki et al. |
| 6,720,644 B2 | 4/2004 | Yoshizawa et al. |
| 6,730,932 B2 | 5/2004 | Yamazaki et al. |
| 6,888,509 B2 * | 5/2005 | Atherton ............ 343/718 |
| 6,913,944 B2 | 7/2005 | Hirai |
| 7,187,961 B2 | 3/2007 | Yamashita et al. |
| 7,230,316 B2 | 6/2007 | Yamazaki et al. |
| 7,354,195 B2 | 4/2008 | Sakano |
| 7,561,052 B2 | 7/2009 | Arai et al. |
| 7,768,391 B2 | 8/2010 | Koyama et al. |
| 8,547,221 B2 * | 10/2013 | Koyama et al. ...... 340/539.12 |
| 2002/0013538 A1 | 1/2002 | Teller |
| 2002/0077673 A1 | 6/2002 | Penner et al. |
| 2002/0094639 A1 | 7/2002 | Reddy |
| 2002/0192886 A1 | 12/2002 | Inoue |
| 2003/0016122 A1 | 1/2003 | Petrick |
| 2004/0000713 A1 | 1/2004 | Yamashita et al. |
| 2004/0164300 A1 | 8/2004 | Yamazaki et al. |
| 2004/0169786 A1 | 9/2004 | Yamazaki et al. |
| 2004/0193020 A1 | 9/2004 | Chiba et al. |
| 2005/0051870 A1 | 3/2005 | Yamazaki et al. |
| 2005/0141591 A1 | 6/2005 | Sakano |
| 2005/0147151 A1 | 7/2005 | Nakazawa et al. |
| 2005/0154327 A1 | 7/2005 | Nakazawa |
| 2005/0163189 A1 | 7/2005 | Nakazawa et al. |
| 2005/0226310 A1 | 10/2005 | Nakazawa et al. |
| 2006/0142819 A1 | 6/2006 | Penner et al. |
| 2008/0015421 A1 | 1/2008 | Penner |
| 2008/0103553 A1 | 5/2008 | Penner et al. |

FOREIGN PATENT DOCUMENTS

| | | |
|---|---|---|
| EP | 1 486 763 | 12/2004 |
| JP | 08-084779 | 4/1996 |
| JP | 08-507698 | 8/1996 |
| JP | 2000-506410 | 5/2000 |
| JP | 2001-307268 | 11/2001 |
| JP | 2004-121632 | 4/2004 |
| JP | 2004-221570 | 8/2004 |
| JP | 2004-241832 | 8/2004 |
| WO | WO 94/04094 | 3/1994 |
| WO | WO 94/06105 | 3/1994 |
| WO | WO 96/22049 | 7/1996 |
| WO | WO 96/22058 | 7/1996 |
| WO | WO 96/39099 | 12/1996 |
| WO | WO 97/33513 | 9/1997 |
| WO | WO 03/020126 | 3/2003 |
| WO | WO 03/078948 | 9/2003 |
| WO | WO 2004042868 A1 * | 5/2004 ............. H01Q 1/38 |

OTHER PUBLICATIONS

Written Opinion (Application No. PCT/JP2005/016373) dated Oct. 25, 2005.

Office Action (Application No. 200580029576.X) dated Aug. 14, 2009.

European Search Report (Application No. 05781930.2) dated Oct. 10, 2012.

* cited by examiner

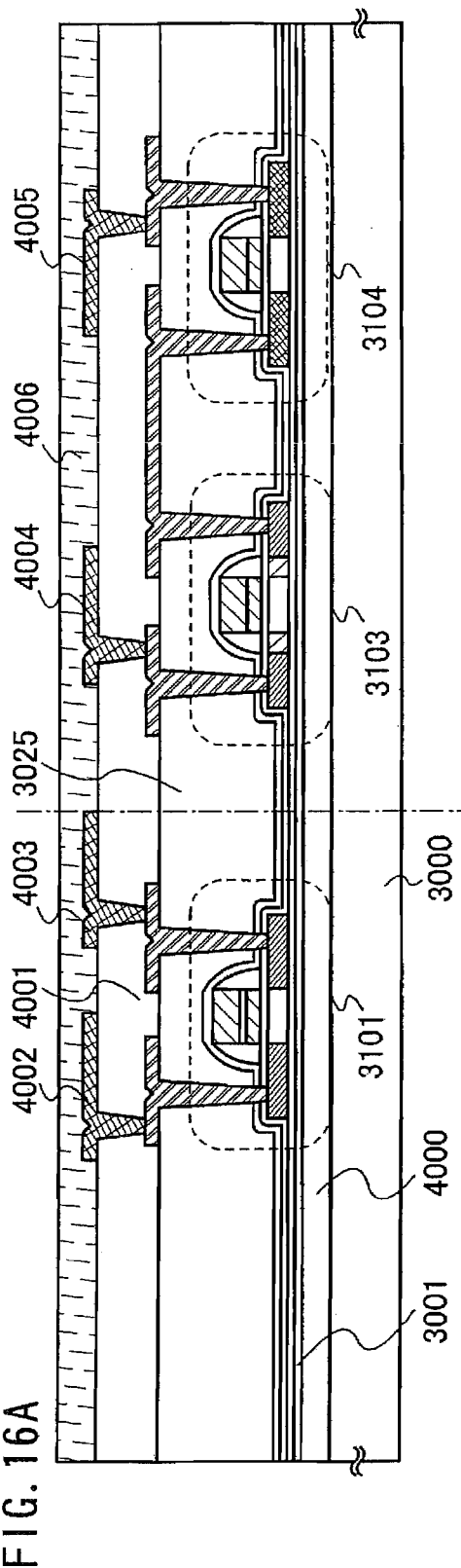
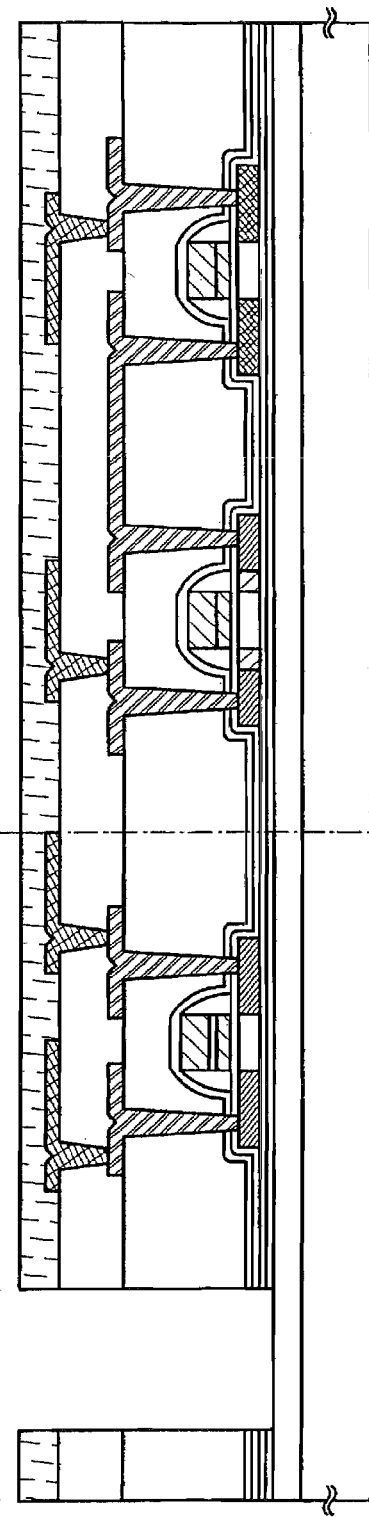
FIG. 16A
FIG. 16B

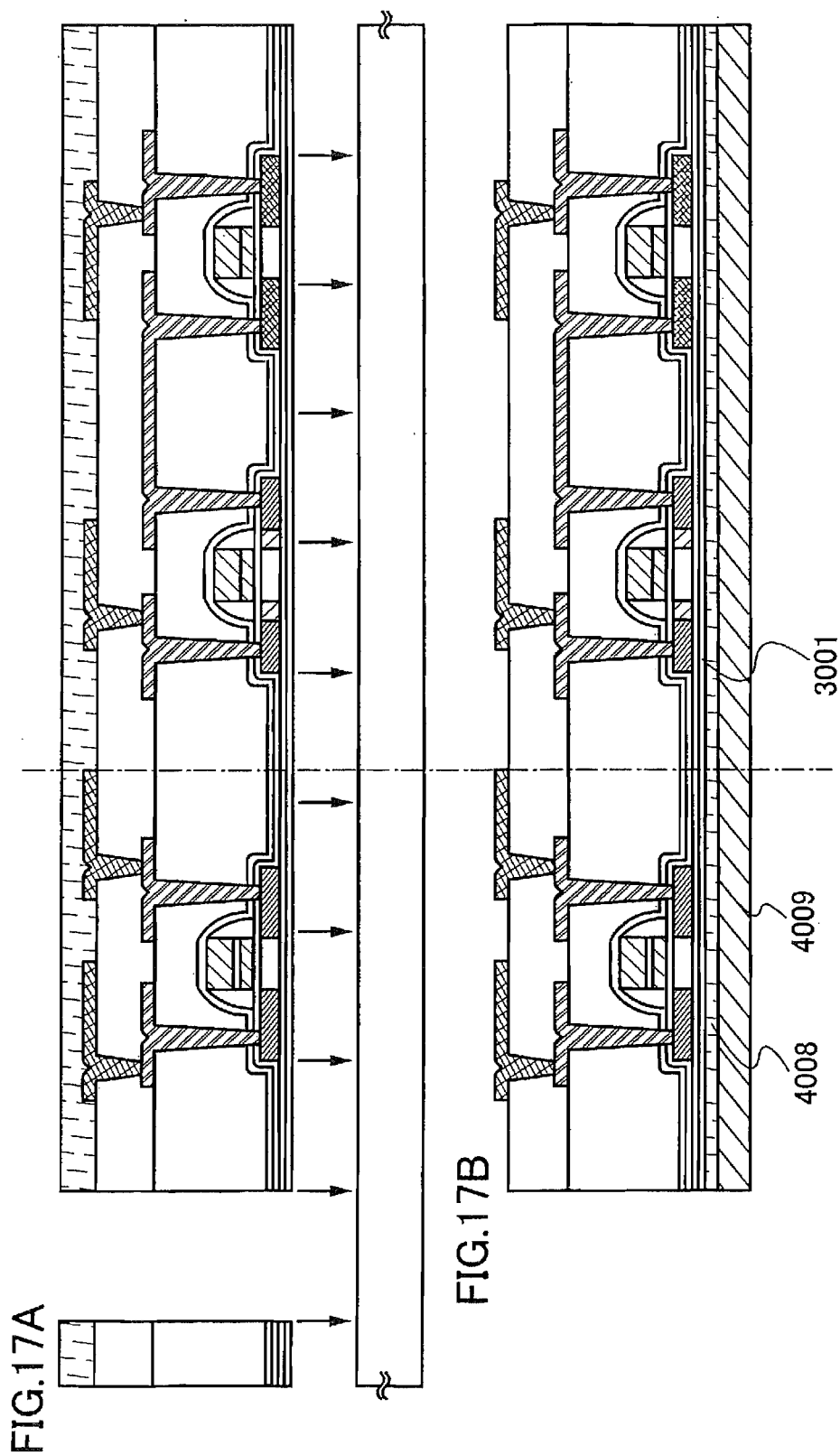

HEALTH DATA COLLECTING SYSTEM AND SEMICONDUCTOR DEVICE

TECHNICAL FIELD

The present invention relates to a semiconductor device using an IC chip (hereinafter referred to as a "wireless chip") by which required data can be read using a non-contact means such as a wireless communication. In particular, the invention relates to a semiconductor device used as a wireless chip formed over an insulating substrate such as glass and plastic.

BACKGROUND ART

At the present time, various data have become to be processed by the development of IT technology. The data management for human health is among them. In companies, schools and the like, for example, health check is regularly carried out and a health condition is informed at least once in a year or half a year. In the case where an abnormality is found out, the corresponding person is notified to be treated at a hospital and the like.

At home also, a simple measurement instrument for health check has been developed by which one's health condition can be easily checked. A portable measurement instrument is widely used in recent years, which contributes to the early detection of diseases.

Examples of such a health condition measurement instrument are disclosed in Patent Document 1 and the like.

PATENT DOCUMENT 1

Japanese Patent Laid-open No. 2004-121632

Patent Document 1 discloses a portable blood pressure measurement instrument. By using such a measurement instrument, health condition can be easily obtained.

DISCLOSURE OF INVENTION

A conventional health measurement instrument described above has following problems. Even though a health measurement instrument has been downsized to some extent, it is still too large to be carried around. Moreover, even when a user obtains data by measurement, he/she tends to be unconscious of the change in his/her physical condition as a medical specialist does not see the data immediately, which results in the progress of disease.

The invention provides a semiconductor device using a wireless chip to solve the aforementioned problems by incorporating or mounting a sensor in the chip and transmitting data from the wireless chip.

The invention comprises a modulating circuit, a logic circuit, a sensor circuit, and an antenna circuit over an insulating substrate. The sensor circuit is operationally connected to the modulating circuit through the logic circuit. The modulating circuit is operationally connected to the antenna circuit.

The invention comprises a modulating circuit, a logic circuit, a sensor circuit, an antenna circuit, and a memory circuit over an insulating substrate. The sensor circuit is operationally connected to the logic circuit through the memory circuit. The logic circuit is operationally connected to the modulating circuit. The modulating circuit is operationally connected to the antenna circuit.

In the aforementioned configurations, the sensor circuit is a pressure sensor.

In the aforementioned configurations, the sensor circuit is an audio sensor.

In the aforementioned configurations, the sensor circuit is an optical sensor.

In the aforementioned configurations, the sensor circuit is an odor sensor.

In the aforementioned configurations, the antenna circuit, the modulating circuit, the logic circuit, and the sensor circuit are provided over the same insulating substrate.

In the aforementioned configurations, the modulating circuit, the logic circuit, and the sensor circuit are integrated over the same insulating substrate while the antenna circuit is provided over another insulating substrate.

In the aforementioned configurations, the modulating circuit and the logic circuit are integrated over the same insulating substrate while the sensor circuit is provided over another insulating substrate.

In the aforementioned configurations, the insulating substrate is a glass substrate.

In the aforementioned configurations, the insulating substrate is a plastic substrate.

In the aforementioned configurations, the insulating substrate is a film insulator.

In the aforementioned configurations, the antenna circuit is provided over at least one of the modulating circuit, the logic circuit, and the sensor circuit.

In the aforementioned configurations, a signal inputted to the antenna circuit is a wireless signal.

In the aforementioned configurations, the semiconductor device is used a health data collecting system.

The invention comprises a health data collecting system comprising a wireless chip including at least a sensor for obtaining biological information data (biological signal and so on), an antenna circuit for transmitting the biological information data, a modulating circuit, and a logic circuit, an interrogator transmitting electromagnetic waves to the wireless chip, and a data system evaluating the biological information data from the wireless chip. The wireless chip is attached to or buried in a living thing. The sensor and an antenna circuit are formed over an flexible substrate, a signal inputted from the antenna is modulated by the modulating circuit and inputted as data to the logic circuit.

In the aforementioned configurations, the health data collecting system further comprising a memory circuit for storing the biological information data over the flexible substrate. The sensor circuit is operationally connected to the logic circuit through the memory circuit. The logic circuit is operationally connected to the modulating circuit.

In the aforementioned configurations, the wireless chip includes at least a thin film transistor.

In the aforementioned configurations, the living thing is human.

As described above, by using the semiconductor device of the invention, data obtained wirelessly can be transmitted. That is, health data obtained through a sensor is transmitted wirelessly and the data is managed by IT technology, which contributes to the early detection, treatment and the like of diseases.

BRIEF DESCRIPTION OF DRAWINGS

FIGS. 16A and 16B are cross sectional diagrams showing steps of the invention.

FIGS. 17A and 17B are cross sectional diagrams showing steps of the invention.

BEST MODE FOR CARRYING OUT THE INVENTION

Figure 1:
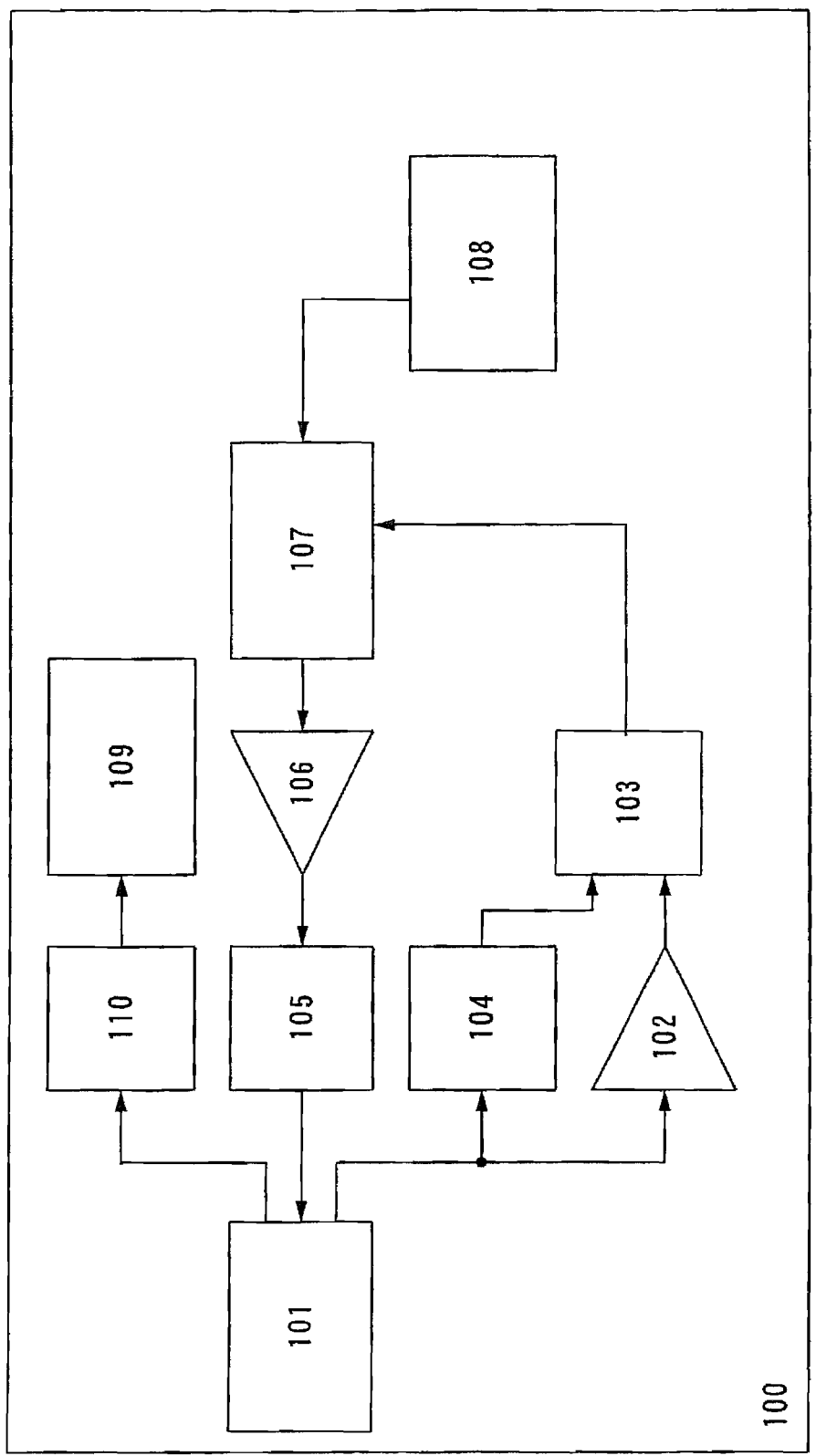
FIG. 1 is a block diagram showing a configuration of a semiconductor device of the invention.

Although the present invention will be fully described by way of embodiment modes and embodiments with reference to the accompanying drawings, it is to be understood that various changes and modifications will be apparent to those skilled in the art. Therefore, unless otherwise such changes and modifications depart from the scope of the present invention, they should be construed as being included therein. Note that identical portions in the drawings are denoted by the same reference numerals and detailed descriptions thereof are omitted.

Figure 3A:
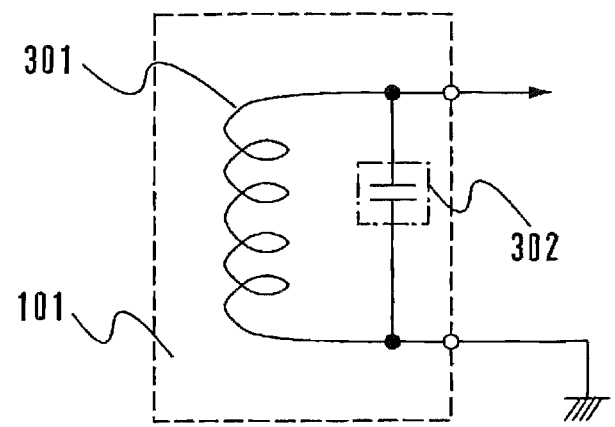
FIGS. 3A and 3B are a block diagram showing an antenna configuration of a semiconductor device of the invention.
Figure 3B:
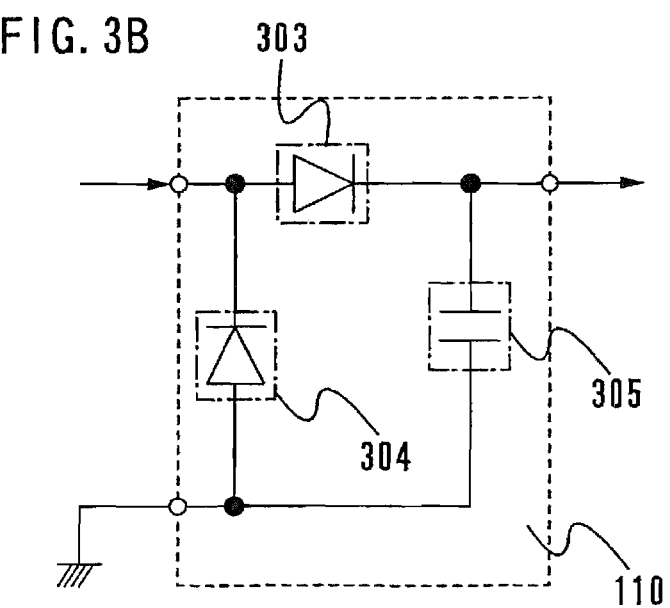

FIG. 1 shows one technique for a wireless chip of the invention. A semiconductor device 100 used for a wireless chip includes an antenna circuit 101, a rectifying circuit 110, a stabilized power supply circuit 109, an amplifier 102, a demodulating circuit 104, an instruction evaluation logic circuit 103, a sensor circuit 108, a logic circuit 107, an amplifier 106, and a modulating circuit 105. Further, the antenna circuit 101 is formed of an antenna coil 301 and a tuning capacitor 302 (FIG. 3A). The rectifying circuit 110 is formed of diodes 303 and 304, and a smoothing capacitor 305 (FIG. 3B).

An operation of such a wireless chip is described below. An AC signal received by the antenna circuit 101 is half-wave rectified by the diodes 303 and 304 and then smoothed by the smoothing capacitor 305. The smoothed voltage containing a number of ripples is stabilized by the stabilized power supply circuit 109, and the stabilized voltage is supplied to the demodulating circuit 104, the amplifier 102, the instruction evaluation logic circuit 103, the amplifier 106, the logic circuit 107, and the sensor circuit 108. On the other hand, a signal received by the antenna circuit 101 is inputted to the instruction evaluation logic circuit 103 as a clock signal through the amplifier 102. Further, a signal inputted from the antenna is demodulated by the demodulating circuit 104 and inputted as data to the instruction evaluation logic circuit 103.

Figure 7:
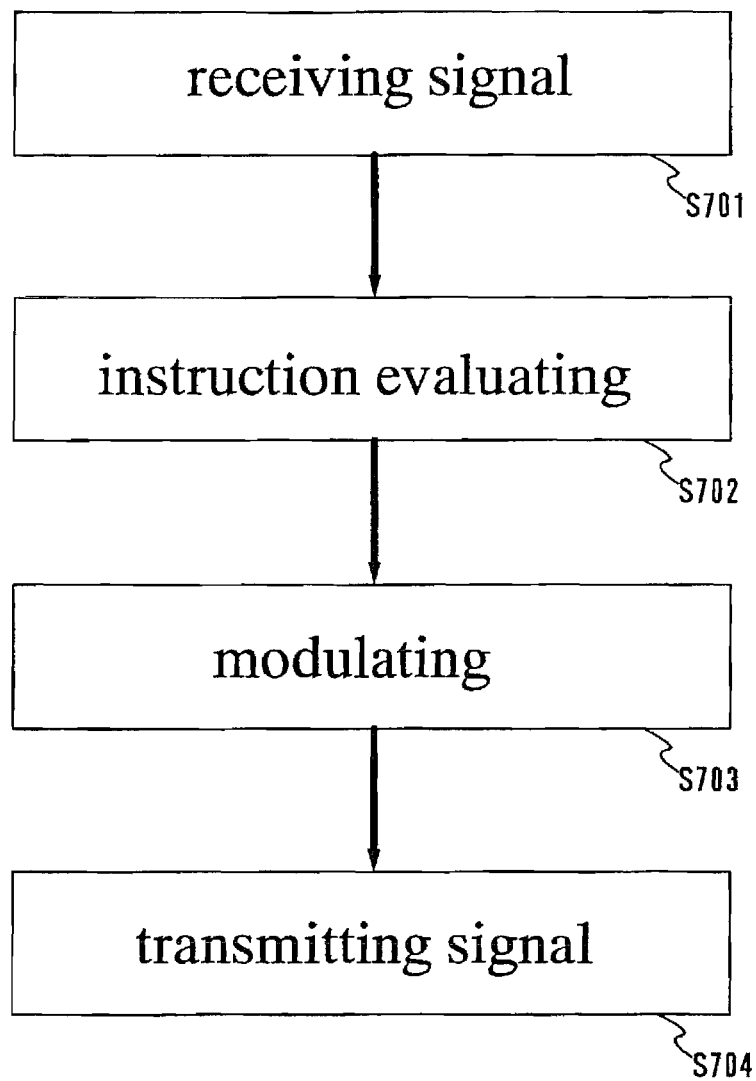
FIG. 7 is a diagram showing an operation flow of a semiconductor device of the invention.

In the instruction evaluation logic circuit 103, the inputted data is decoded. An interrogator transmits data by encoding with a deformation mirror code, an NRZ-L code, or the like, and then the encoded data is decoded by the instruction evaluation logic circuit 103. The decoded data is transmitted to the logic circuit 107, thereby sensed biological data in the sensor circuit 108 is calculated. The result of the calculation is modulated by the modulating circuit 105 through the amplifier 106 and outputted from the antenna circuit 101. This flow is shown in FIG. 7. This flow chart outlining operating procedure S700 is shown in FIG. 7. Operating procedure S700 begins when a wireless chip receives a signal (S701). The first step is instruction evaluating step (S702). The second step is modulating step (S703). The third step is transmitting signal (including biological information) step (S704).

In this embodiment mode, the antenna circuit 101 is formed over the semiconductor device 100, however, the invention is not limited to this and the antenna circuit may be connected externally to the semiconductor device. The sensor may be a pressure sensor, an optical sensor, an odor sensor, or an audio sensor.

Figure 2:
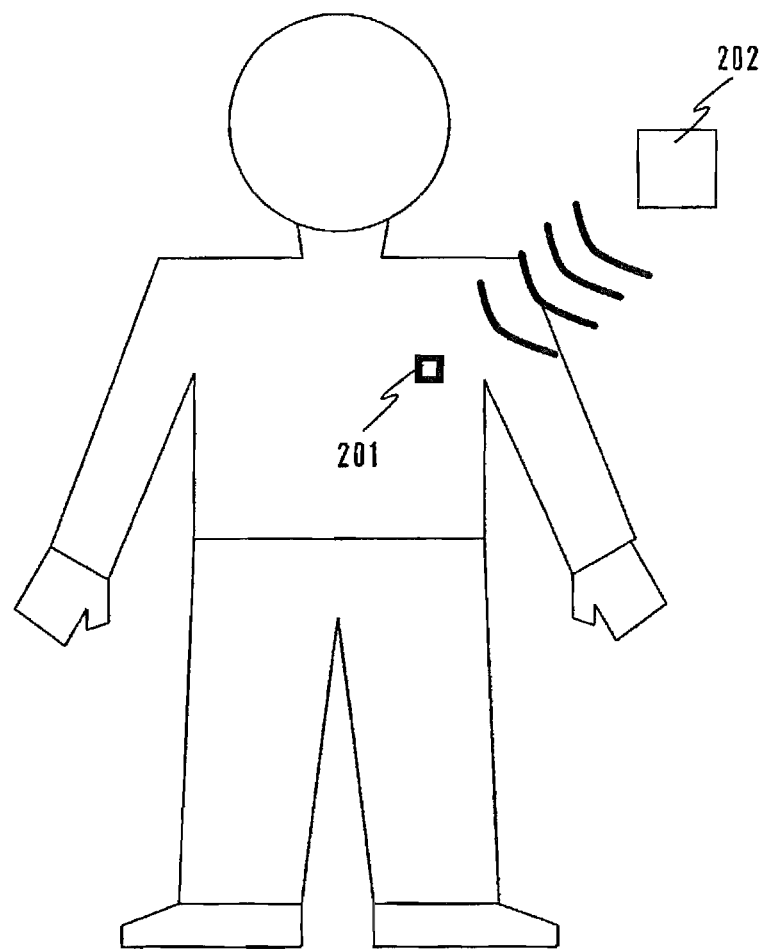
FIG. 2 is a diagram showing an application to a human body.

The outline of a health data collecting system using a wireless chip is described with reference to FIG. 2. FIG. 2 shows an outline of the health data collecting system made for wirelessly obtaining human health data (also referred to as biological information, vital information, or living body information). A wireless chip 201 is attached to or buried (implanted) in one of a human body and an animal body. An interrogator (also referred to as a reader/writer) 202 transmits electromagnetic waves to the wireless chip. Receiving the electromagnetic waves, the wireless chip 201 transmits data obtained by the sensor circuit therein back to the interrogator 202. The interrogator 202 is connected to a data system (not shown) and evaluates the data from the wireless chip. In this manner, human health data can be obtained without carrying a measurement instrument. Moreover, as data is automatically evaluated, it can be prevented that diseases progress due to the delay of notification.

Figure 4:
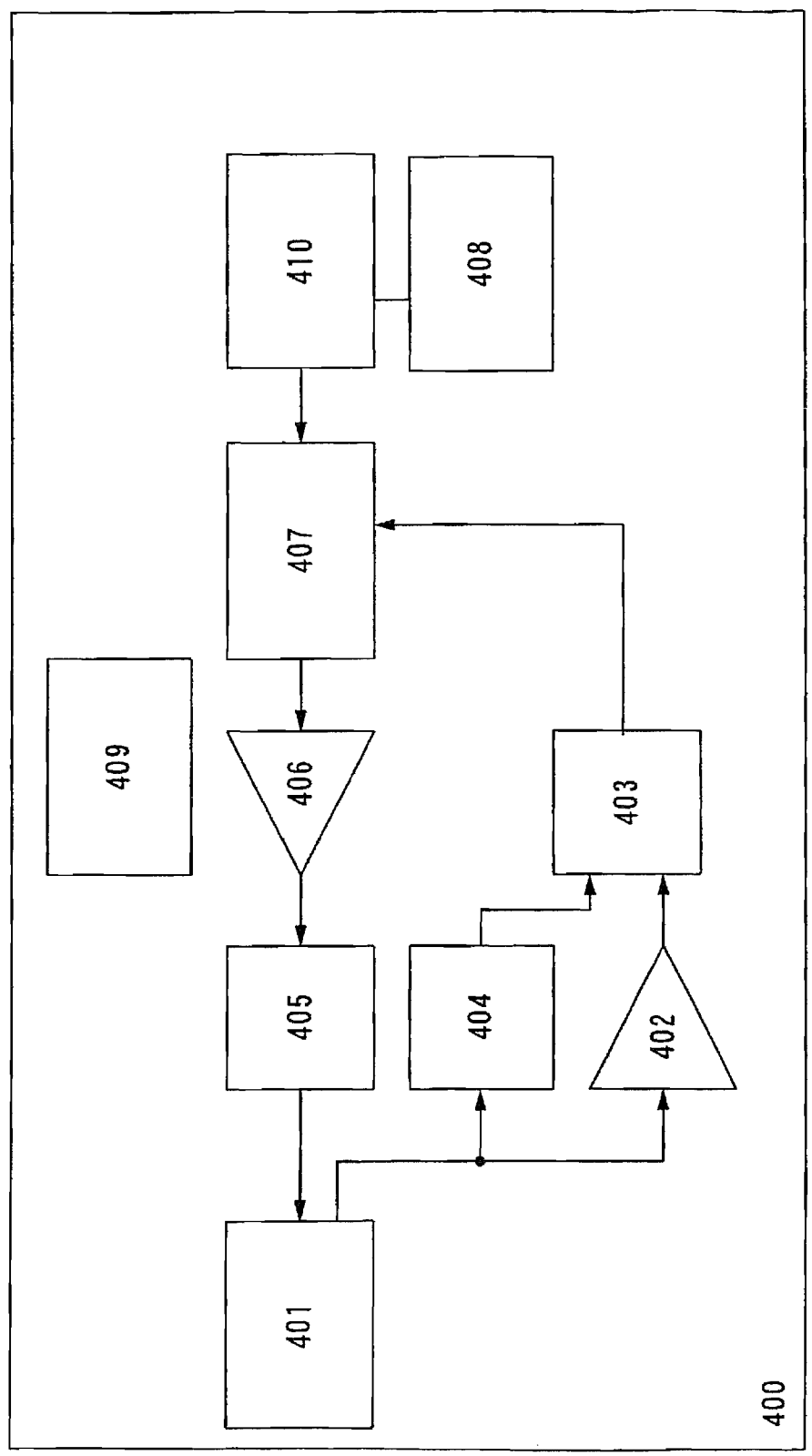
FIG. 4 is a block diagram showing a configuration of a semiconductor device of the invention.

Embodiment Mode 2 of the invention is shown in FIG. 4. A semiconductor device 400 used for a wireless chip includes an antenna circuit 401, a battery 409, an amplifier 402, a demodulating circuit 404, an instruction evaluation logic circuit 403, a sensor circuit 408, a logic circuit 407, an amplifier 406, a modulating circuit 405, and a memory circuit 410. The antenna circuit 401 is formed of an antenna coil and a tuning capacitor similarly to the antenna circuit shown in FIG. 3A.

An operation of such a wireless chip is described below. In this embodiment mode, a power is supplied by the battery 409 which is incorporated. A signal received by the antenna circuit 401 is inputted as a clock signal to the instruction evaluation logic circuit 403 through the amplifier 402. Further, a signal inputted from the antenna is demodulated by the demodulating circuit 404 and inputted as data to the instruction evaluation logic circuit 403.

Figure 6:
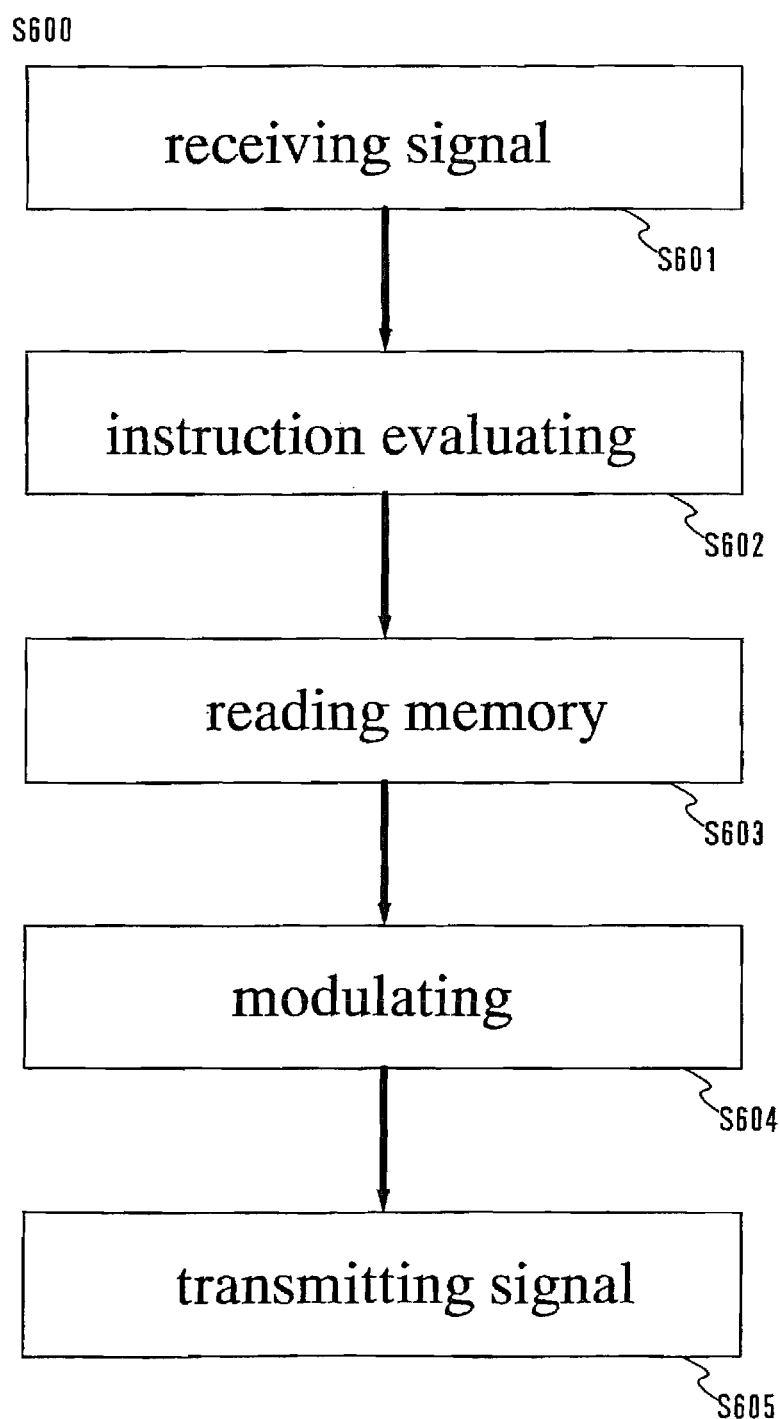
FIG. 6 is a diagram showing an operation flow of a semiconductor device of the invention.

In the instruction evaluation logic circuit 403, the inputted data is decoded. An interrogator transmits data by encoding with a deformation mirror code, an NRZ-L code, or the like, and then the encoded data is decoded by the instruction evaluation logic circuit 403. The decoded data is transmitted to the logic circuit 407, thereby stored biological collection data in the memory circuit 410 is calculated. The result of the calculation is modulated by the modulating circuit 405 through the amplifier 406 and outputted from the antenna circuit 401. Here, the biological data obtained by the sensor circuit 408 is stored in the memory circuit 410. As the battery is incorporated in this embodiment mode, the sensor circuit 408 and the memory circuit 410 can operate even without the interrogator. This flow chart outlining operating procedure S600 is shown in FIG. 6. Operating procedure S600 begins when a wireless chip receives a signal (S601). The first step is instruction evaluating step (S602). The second step is reading memory step (S603). The third step is modulating step (S604). The forth step is transmitting signal (including biological information) step (S605).

In this embodiment mode, the antenna circuit 401 and the battery 409 are formed in the semiconductor device 400, however, the invention is not limited to this and the antenna circuit 401 and the battery 409 may be connected externally to the semiconductor device 400. The communication with the interrogator is as described above. The sensor may be a pressure sensor, an optical sensor, an odor sensor, or an audio sensor.

[Embodiment 1]

Figure 5:
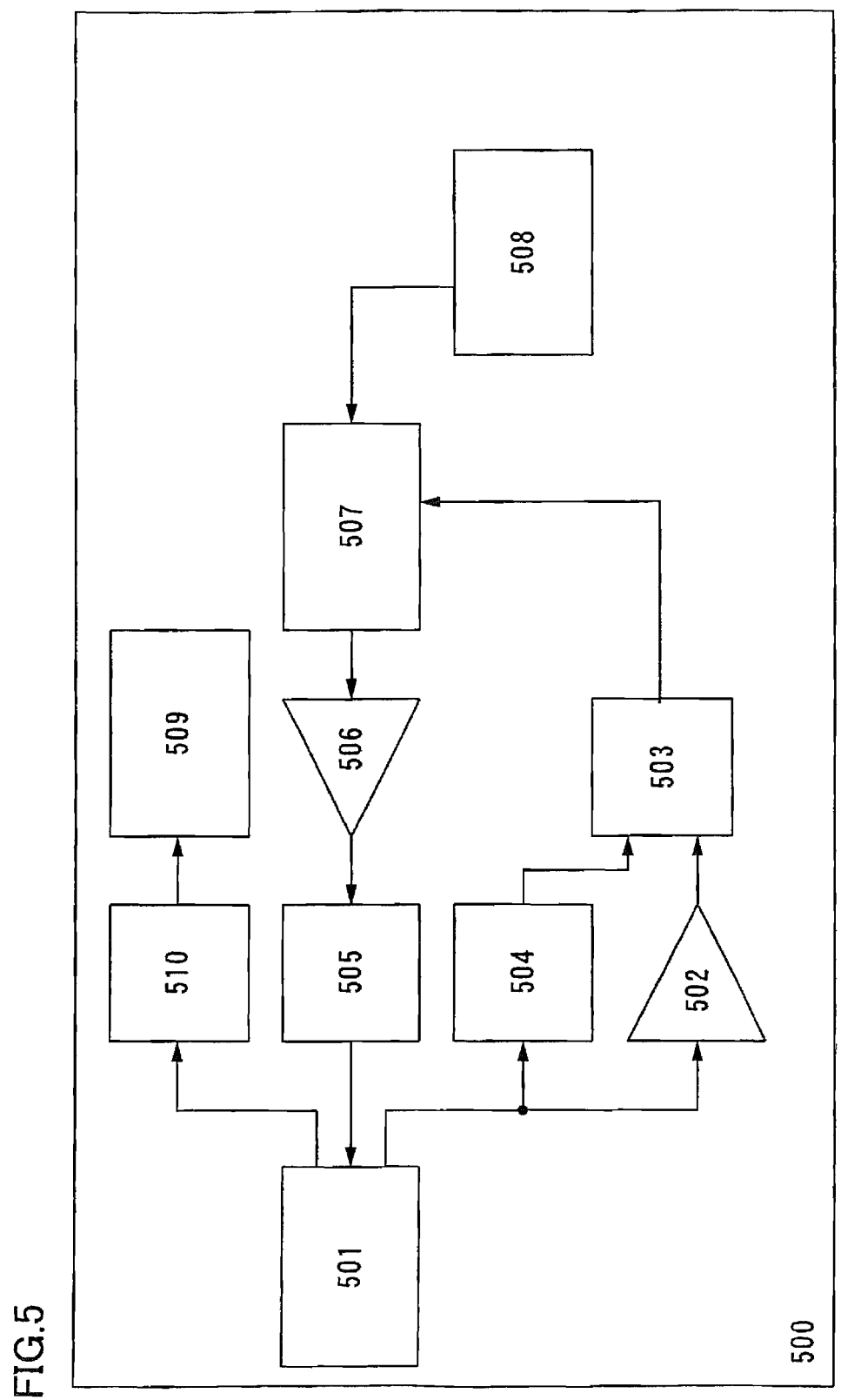
FIG. 5 is a block diagram showing a configuration of a semiconductor device of the invention.

FIG. 5 shows an embodiment of a wireless chip of the invention. Data on pulses and blood pressure of human can be obtained by providing a pressure sensor near a heart or a blood vessel. In this embodiment mode, a pressure sensor is provided for a wireless chip. A semiconductor device 500 used for a wireless chip includes an antenna circuit 501, a rectifying circuit 510, a stable power source circuit 509, an amplifier 502, a demodulating circuit 504, an instruction evaluation logic circuit 503, a pressure sensor circuit 508, a logic circuit 507, an amplifier 506, and a modulating circuit 505. The antenna circuit 501 is formed of an antenna coil and a tuning capacitor similarly to the antenna circuit shown in FIG. 3A. The rectifying circuit 510 is formed of a diode and a smoothing capacitor similarly to the rectifying circuit shown in FIG. 3B.

An operation of such a wireless chip is described below. An AC signal received by the antenna circuit 501 is half-wave rectified by the diodes 303 and 304 and then smoothed by the smoothing capacitor 305. The smoothed voltage containing a number of ripples is stabilized by the stabilized power supply circuit 509, and the stabilized voltage is supplied to the demodulating circuit 504, the amplifier 502, the instruction evaluation logic circuit 503, the amplifier 506, the logic circuit 507, and the pressure sensor circuit 508. On the other hand, a signal received by the antenna circuit 501 is inputted to the instruction evaluation logic circuit 503 as a clock signal through the amplifier 502. Further, a signal inputted from the antenna circuit 501 is demodulated by the demodulating circuit 504 and inputted as data to the instruction evaluation logic circuit 503.

In the instruction evaluation logic circuit 503, the inputted data is decoded. An interrogator transmits data by encoding with a deformation mirror code, an NRZ-L code, or the like, and then the encoded data is decoded by the instruction evaluation logic circuit 503. The decoded data is transmitted to the logic circuit 507, thereby sensed data in the pressure sensor circuit 508 is calculated. The result of the calculation is modulated by the modulating circuit 505 through the amplifier 506 and outputted from the antenna circuit 501. In this embodiment mode, the antenna circuit 501 is formed in the semiconductor device 500, however, the invention is not limited to this and the antenna circuit 501 may be connected externally to the semiconductor device 500.

[Embodiment 2]

Figure 8:
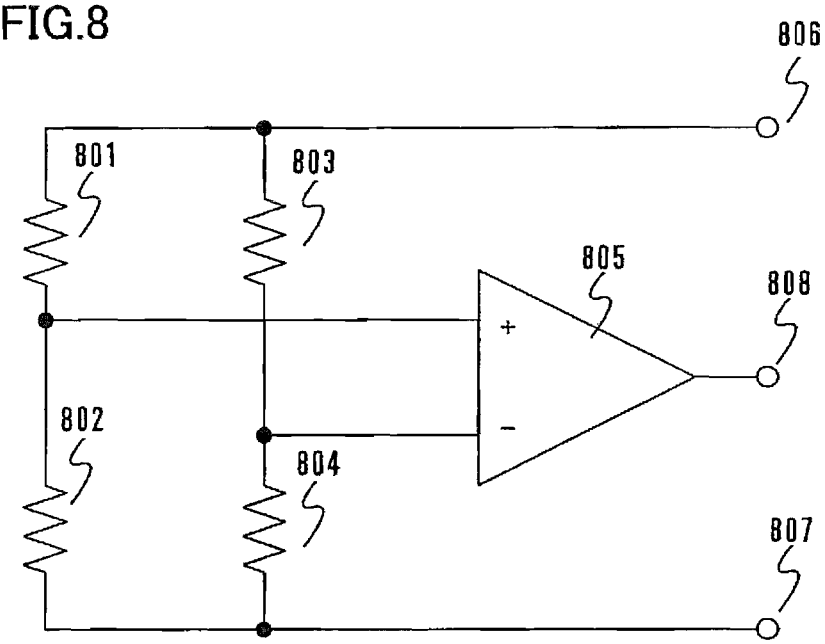
FIG. 8 is a diagram showing a pressure sensor circuit used for the invention.

FIG. 8 shows an embodiment of a pressure sensor circuit. The pressure sensor circuit of this embodiment is formed of semiconductor resistors 801 to 804, a differential amplifier 805, power source terminals 806 and 807, and an output terminal 808. In general, when a semiconductor resistor receives a stress, resistance thereof changes by piezoelectric effect. In the pressure sensor of this embodiment mode, the semiconductor resistors 801 to 804 are arranged at different positions so that a different stress is generated at each of the resistors when a pressure is applied. When a pressure is applied, two input voltages of the differential amplifier change. By changing the input voltages, a pressure can be sensed. By amplifying this pressure sensor in the aforementioned wireless chip, data obtained by the sensor can be transmitted wirelessly. It is to be noted that the pressure sensor of the invention is not limited to the circuit of this embodiment and other circuits may be employed as well. Further, a sensor may be any one of a pressure sensor, an optical sensor, an odor sensor, or an audio sensor.

[Embodiment 3]

A method for manufacturing a memory element and TFTs used for a logic circuit portion such as a decoder, a selector, a write circuit, and a read circuit over an insulating substrate at the same time is described with reference to FIG. 15. It is to be noted that an n-channel memory element having a floating gate, an n-channel TFT, and a p-channel TFT are described as examples of a semiconductor element in this embodiment, however, the semiconductor element included in the memory portion and logic circuit portion of the invention is not limited to these. Further, this manufacturing method is only an example and does not limit a manufacturing method over the insulating substrate.

First, base films 3001 and 3002 formed of an insulating film such as a silicon oxide film, a silicon nitride film, or a silicon oxynitride film are formed over a glass substrate 3000. For example, a silicon oxynitride film is formed as the base film 3001 with a thickness of 10 to 200 nm, and a silicon oxynitride hydrogenated film is formed as the base film 3002 with a thickness of 50 to 200 nm.

Island-shaped semiconductor layers 3003 to 3005 are formed of crystalline semiconductor films formed by crystallizing a semiconductor film having an amorphous structure by known laser or thermal crystallization. Each of these island-shaped semiconductor layers 3003 to 3005 is formed with a thickness of 25 to 80 nm. A material for the crystalline semiconductor film is not particularly limited, however, silicon or silicon germanium (SiGe) alloy is preferable.

Here, a process for providing an overlapping region may be carried out for extracting a charge on one side of a source region or a drain region of the semiconductor layer 3003 of the TFT used for the memory element.

Subsequently, a gate insulating film 3006 to cover the island-shaped semiconductor layers 3003 to 3005 is formed. The gate insulating film 3006 is formed of an insulating film containing silicon with a thickness of 10 to 80 nm by plasma CVD or sputtering. In particular, an OTP type nonvolatile memory which requires writing by hot electron injection and holding of a charge is preferably formed with a thickness of 40 to 80 nm which does not easily generate a tunnel current.

Then, first conductive layers 3007 to 3009 are formed over the gate insulating film 3006 and removed by etching except for a region including a region to be a floating gate electrode and a region to be a normal gate electrode of a TFT.

Subsequently, a second gate insulating film 3010 is formed. The second gate insulating film 3010 is formed of an insulating film containing silicon with a thickness of 10 to 80 nm by plasma CVD or sputtering. The gate insulating film 3006 is removed by etching except for a region including a memory element.

Subsequently, second conductive layers 3011 to 3013 are formed and a stack (memory element) of the first conductive layer 3007, the second gate insulating film 3010, and the second conductive layer 3011 or a stack (TFT) of the first conductive layer 3007 and the second conductive layer 3011 are etched together to form a floating gate electrode and a control gate electrode of the memory element and a gate electrode of the TFT.

In this embodiment mode, the first conductive layers 3007 to 3009 are formed of TaN with a thickness of 50 to 100 nm and the second conductive layers 3011 to 3013 are formed of W with a thickness of 100 to 300 nm, however, a material for the conductive layer is not particularly limited. An element selected from Ta, W, Ti, Mo, Al, Cu, and the like, an alloy material or a compound material containing the aforementioned element as a main component may be used as well.

Subsequently, doping is carried out for imparting n-type conductivity to the TFT used for the memory element, thereby first impurity regions 3014 and 3015 are formed. Next, doping is carried out for imparting p-type conductivity to a p-channel TFT used for the logic circuit portion, thereby second impurity regions 3016 and 3017 are formed. Subsequently, doping is carried out for imparting n-type conductivity for forming an LDD region of an n-channel TFT used for the logic circuit portion, thereby third impurity regions 3018 and 3019 are formed. After that, side walls 3020 and 3021 are formed and doping is carried out for imparting n-type conductivity to the n0channel TFT used in the logic circuit portion, thereby fourth impurity regions 3022 and 3023 are formed. These doping may be carried out by ion doping or ion injection. By the aforementioned steps, impurity regions are formed in each of the island-shaped semiconductor layers.

Subsequently, a step for activating an impurity element added to each of the island-shaped semiconductor layers is performed. This step is carried out by thermal annealing using an annealing furnace. Alternatively, laser annealing or rapid thermal annealing (RTA) can be applied as well. Further, thermal treatment is performed in an atmosphere containing hydrogen by 3 to 100% at 300 to 450° C. for 1 to 12 hours, thereby the island-shaped semiconductor layers are hydrogenated. Alternatively, the island-shaped semiconductor layer may be hydrogenated by plasma hydrogenation (using hydrogen excited by plasma).

Subsequently, a first interlayer insulating film 3024 is formed of a silicon oxynitride film. The first interlayer insulating film 3024 is formed with a thickness of 10 to 80 nm which is approximately the same thickness as the gate insulating film. Next, a second interlayer insulating film 3025 is formed of an organic insulating material such as acrylic. Further, an inorganic material can be used for the second interlayer insulating film 3025 instead of using an organic insulating material. As an inorganic material, inorganic $SiO_2$, $SiO_2$ formed by plasma CVD (PCVD-$SiO_2$), SOG (Spin On Glass; coated silicon oxide film) and the like are used. An etching step for forming a contact hole is performed after forming the two interlayer insulating films.

Then, electrodes 3026 and 3027 are formed to be in contact with a source region and drain region of the island-shaped semiconductor layers in the memory portion. In the logic circuit portion as well, electrodes 3028 to 3030 are formed.

Figure 15:
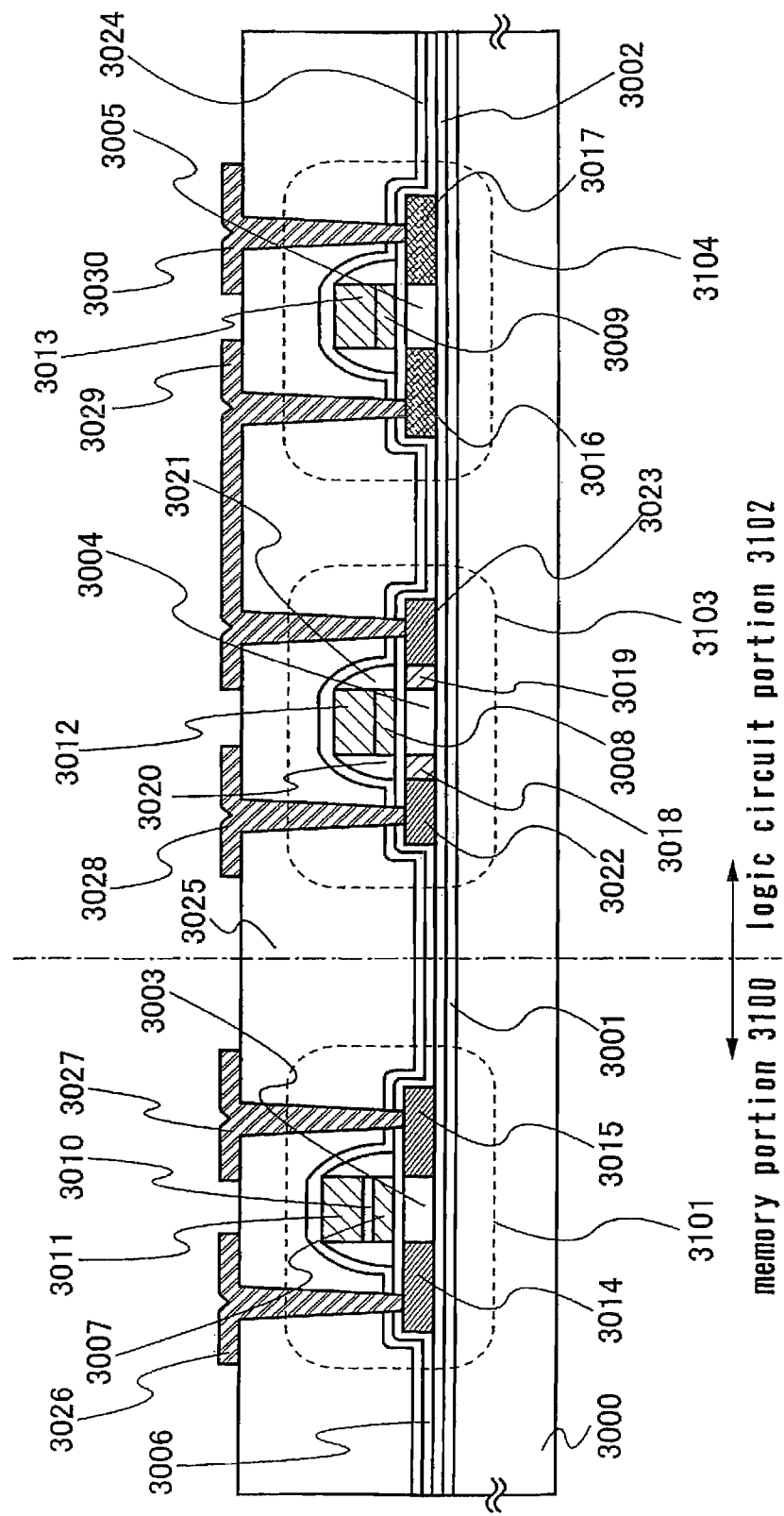
FIG. 15 is a diagram showing a step of the invention.

As described above, the memory portion 3100 including the n-channel memory element 3101 having the floating gate and the logic circuit portion 3102 including the n-channel TFT 3103 having the LDD structure and the p-channel TFT 3104 having the single-drain structure can be formed over the same substrate (see FIG. 15).

[Embodiment 4]

In this embodiment, description is made with reference to FIGS. 16A to 17B on a manufacturing method for forming a memory portion and a logic circuit portion and transferring them to a flexible substrate. It is to be noted that an n-channel memory element having a floating gate, an n-channel TFT, and a p-channel TFT are taken as an example, however, semiconductor elements included in the memory portion and logic circuit portion of the invention are not limited to these. Further, this manufacturing method is only an example and does not limit a manufacturing method over the insulating substrate.

A peeling layer 4000 is formed over the insulating substrate 3000. The peeling layer 4000 can be formed of a layer containing silicon as a main component such as amorphous silicon, polycrystalline silicon, single crystalline silicon and microcrystalline silicon (including semi-amorphous silicon). The peeling layer 4000 can be formed by sputtering, plasma CVD and the like. In this embodiment, an amorphous silicon film is formed with a thickness of about 500 nm by sputtering as the peeling layer 4000. Subsequently, the memory portion and logic circuit portion as shown in FIG. 15 are formed according to the manufacturing steps described in Embodiment 3.

Subsequently, a third interlayer insulating film 4001 is formed over the second interlayer insulating film 3025, and pads 4002 to 4005 are formed. The pads 4002 to 4005 can be formed using a conductive material containing one or a plurality of metals such as Ag, Au, Cu, Pd, Cr, Mo, Ti, Ta, W, and Al, or a metal compound thereof.

Then, a protective layer 4006 is formed over the third interlayer insulating film 4001 so as to cover the pads 4002 to 4005. The protective layer 4006 is formed of a material capable of protecting the pads 4002 to 4005 when removing the peeling layer 4000 by etching. For example, the protective layer 4006 can be formed by applying an epoxy based, acrylate based, or silicon based resin which is soluble to water or alcohols (see FIG. 16A).

Subsequently, a groove 4007 for separating the peeling layer 4000 is formed (see FIG. 16B). The groove 4007 may be formed at least to expose the peeling layer 4000. The groove 4007 is formed by etching, dicing, scribing and the like.

Subsequently, the peeling layer 4000 is removed by etching (see FIG. 17A).

In this embodiment, halogen fluoride is used as an etching gas which is inlet through the groove 4007. In this embodiment, for example, etching is performed by using $ClF_3$ (chlorine trifluoride) at 350° C. at a flow rate of 300 sccm with a pressure of 6 Torr for three hours. Further, a $ClF_3$ gas mixed with nitrogen may be used as well. By using halogen fluoride such as $ClF_3$, the peeling layer 4000 is selectively etched to peel off the insulating substrate 3000. It is to be noted that halogen fluoride may be a gas or liquid.

Subsequently, the memory portion and the logic circuit portion which are peeled off are attached to a support base 4009 with an adhesive 4008 (see FIG. 17B). A material which can attach the support base 4009 and the base film 3001 is used for the adhesive 4008. For example, various curable adhesives such as a reaction curable adhesive, a heat curable adhesive, an optical curable adhesive such as an ultraviolet curable adhesive, and an anaerobiotic adhesive can be used as the adhesive 4008.

As the support base 4009, an organic material such as a flexible paper or plastic can be used. Alternatively, a flexible inorganic material may be used as the support base 4009. It is preferable that the support base 4009 have a heat conductivity as high as 2 to 30 W/mK for dispersing heat generated at the integrated circuit.

It is to be noted that the integrated circuit including the memory portion and the logic circuit portion may be peeled off the insulating substrate 3000 by various methods as well as by etching a silicon film as described in this embodiment. For example, a metal oxide film is provided between a substrate having high heat resistance and the integrated circuit and the metal oxide film is made vulnerable by crystallization, thereby the integrated circuit can be peeled off. Further, for example, the peeling layer is broken by laser light irradiation to peel the integrated circuit off the substrate. Moreover, for example, the integrated circuit can be peeled off the substrate by mechanically removing the substrate over which the integrated circuit is formed or removing by etching with a solution or a gas.

In the case where an object has a curved surface and thus a support base of an ID chip attached thereto is bent so as to have a curvature along a generating line of a conical surface, a columnar surface and the like, it is preferable that the direction of the generating line and a direction that carriers of a TFT move be the same. By the aforementioned structure, it can be prevented that characteristics of a TFT are affected when the support base is bent. Further, when the island-shaped semiconductor film occupies 1 to 30% of an area of the integrated circuit, it can further be prevented that the characteristics of a TFT are affected when the support base is bent. This embodiment can be implemented in combination with the aforementioned embodiment modes and the other embodiments.

[Embodiment 5]

Figure 18A:
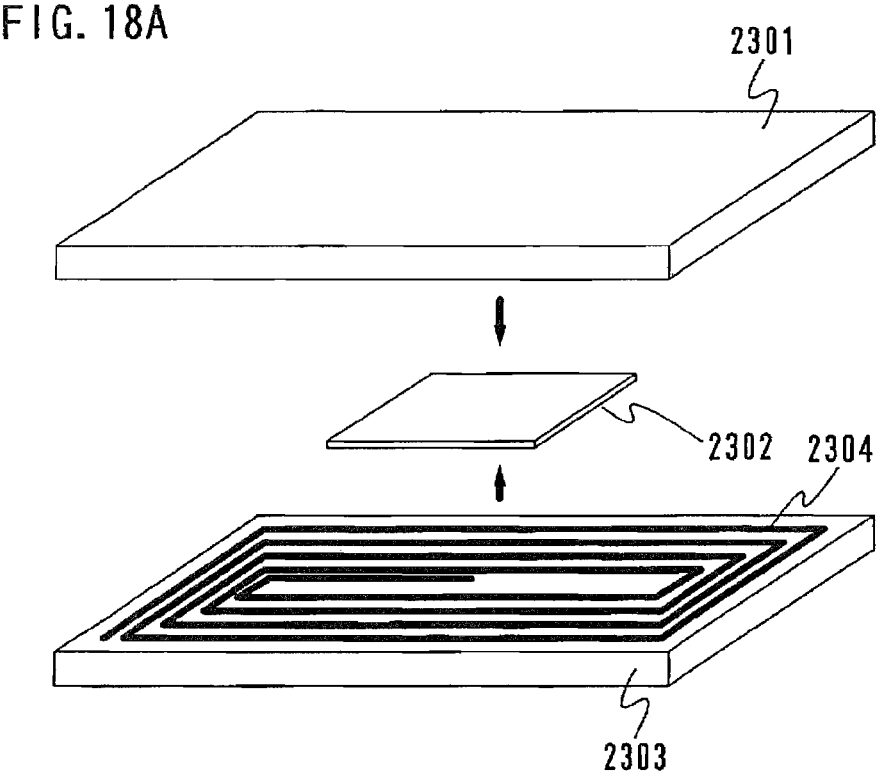
FIGS. 18A and 18B are diagrams in which a semiconductor device of the invention and a protective layer are combined.

An example of forming a flexible wireless chip by a peeling process is described with reference to FIG. 18. The wireless chip is structured by flexible protective layers 2301 and 2303, and a wireless chip 2302 formed by a peeling process. In this embodiment, an antenna 2304 is not formed over the wireless chip 2302 but over the flexible protective layer 2303 and is electrically connected to the wireless chip 2302. In FIG. 18A, the antenna 2304 is formed only over the flexible protective layer 2303, however, it may be formed over the flexible protective layer 2301 as well. The antenna is preferably formed of silver, copper, or a metal plated by them. The wireless chip 2302 and the antenna are connected by an anisotropic conductive film and UV treatment, however, the invention is not limited to this.

Figure 18B:
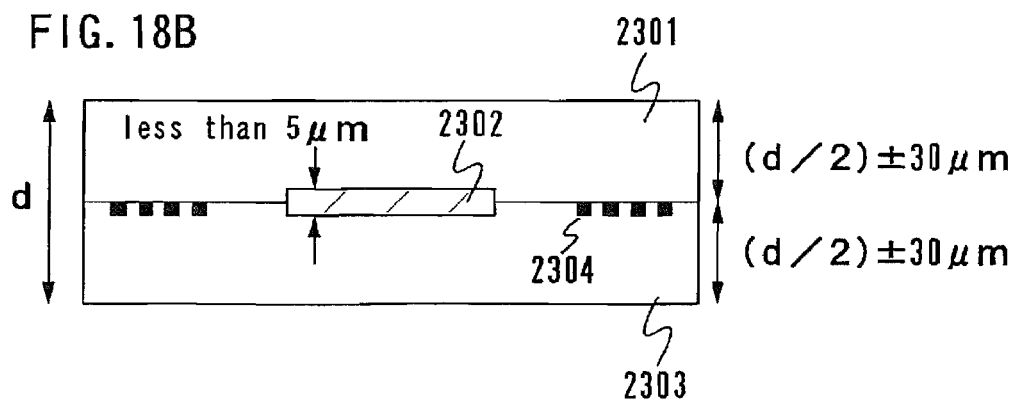

FIG. 18B shows a cross section of FIG. 18A. The wireless chip 2302 has a thickness of 5 μm or less, and preferably 0.1 to 3 μm. Further, each of the flexible protective layers 2301 and 2303 preferably has a thickness of (d/2)±30 μm and more preferably (d/2)±10 μm when the thickness of the stacked flexible protective layers 2301 and 2303 is d. It is preferable that the flexible protective layers 2301 and 2303 have a thickness of 10 to 200 μm. The wireless chip 2302 has an area of 5 mm square or smaller, or preferably 0.3 to 4 mm square.

Each of the flexible protective layers 2301 and 2303 is formed of an organic resin material and has a structure having high resistance against bending. As the wireless chip 2302 itself which is formed by a peeling process is highly resistant against bending, therefore, the wireless chip 2302 can be closely attached to the flexible protective layers 2301 and 2303. The wireless chip surrounded by the flexible protective layers 2301 and 2303 may be provided over or inside another object. Further, the wireless chip may be mounted in a paper.

[Embodiment 6]

Figure 9:
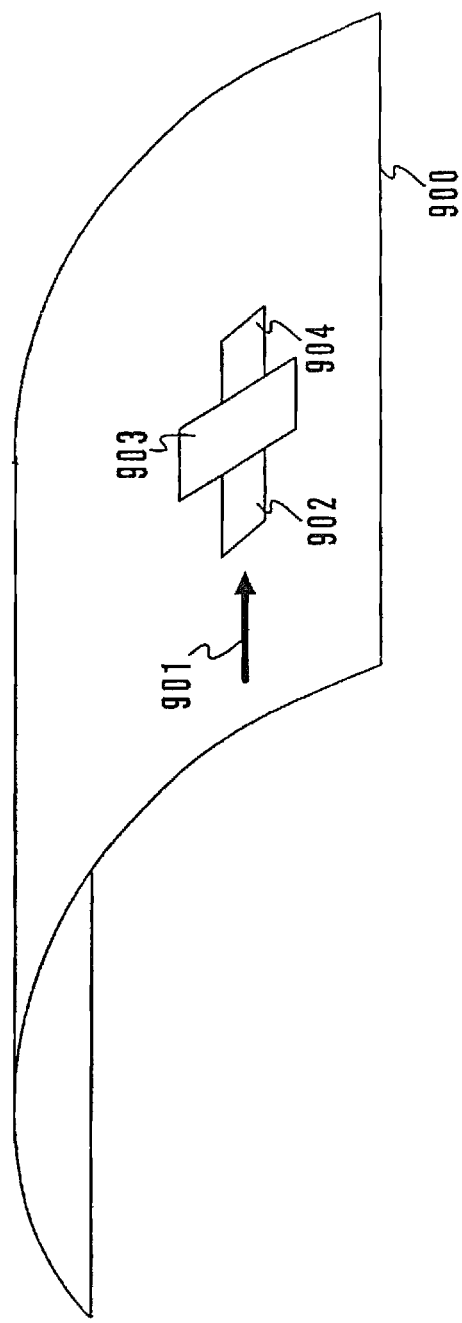
FIG. 9 is a diagram showing an arrangement of TFTs in the invention.

Description is made with reference to FIG. 9 on the case of attaching a wireless chip to a curved surface 900, that is the case of arranging a TFT perpendicularly to a curving direction of the wireless chip. A TFT included in the wireless chip of FIG. 9 is arranged in a direction of current flow 901, that is, a drain electrode 902, a gate electrode 903, and a source electrode 904 are arranged on the same straight line so that an effect of stress becomes less. With such an arrangement, variations in characteristics of TFTs can be suppressed. Further, crystals which form the TFT are aligned in the direction of current flow. By forming the crystals using CWLC and the like, an S value can be set at 0.35 V/dec or smaller (preferably 0.09 to 0.25 V/dec) and mobility can be set at 100 cm$^2$/Vs or higher. In the case of forming a 19-step ring oscillator using such TFTs, an oscillating frequency thereof is 1 MHz or higher, or preferably 100 MHz or higher with a power source voltage of 3 to 5 V. With the power source voltage of 3 to 5 V, delay time of one stage of inverter is 26 ns, and preferably 0.26 ns or less.

Further, it is preferable that an active region (silicon island portion) of an active element such as a TFT occupies 5 to 50% of an entire area in order not to break the active element due to stress. In a region where the active element such as a TFT does not exist, a base insulating material, an interlayer insulating material and a wiring material are mainly provided. It is preferable that an area except for the active region of the TFT is 60% or larger of an entire area. An active region of the active element has a thickness of 20 to 200 nm, typically 40 to 170 nm, and more preferably 45 to 55 nm and 145 to 155 nm.

[Embodiment 7]

In this embodiment, description is made with reference to FIGS. 10A to 11C on an example of providing an external antenna to a circuit using the invention.

Figure 10A:
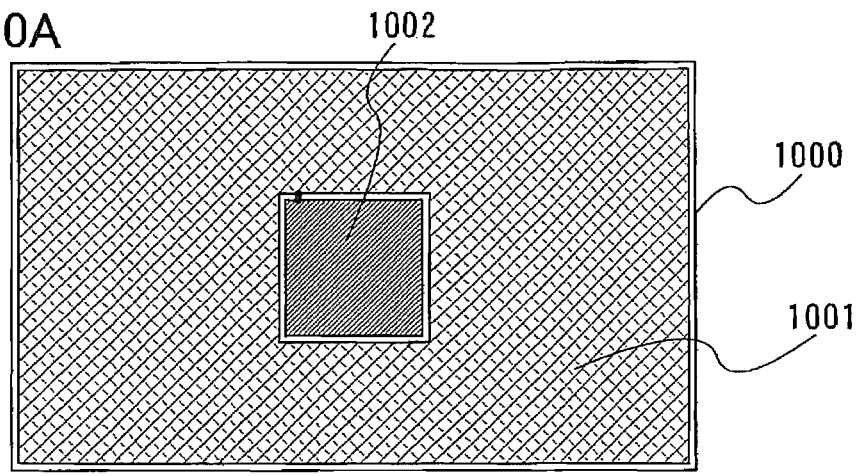
FIGS. 10A to 10E are diagrams showing embodiments of an antenna of the invention.

FIG. 10A shows a circuit of which periphery is covered with an antenna. An antenna 1001 is formed over a substrate 1000 and a circuit 1002 using the invention is connected thereto. In FIG. 10A, the antenna 1001 covers the periphery of the circuit 1002, however, the antenna may cover the entire substrate and the circuit 1002 having electrodes may be attached thereto.

Figure 10B:
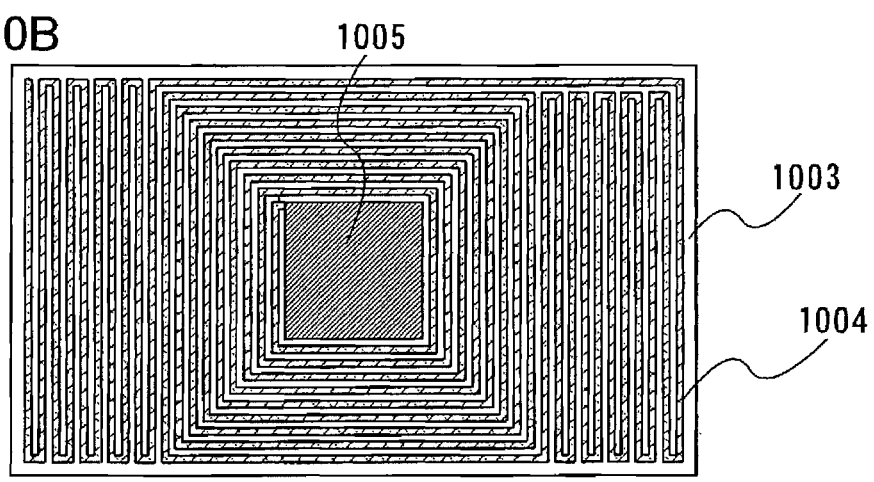

FIG. 10B shows a thin antenna arranged around a circuit. An antenna 1004 is formed over a substrate 1003 and a circuit 1005 using the invention is connected thereto. It is to be noted that the arrangement of antenna is only an example and the invention is not limited to this.

Figure 10C:
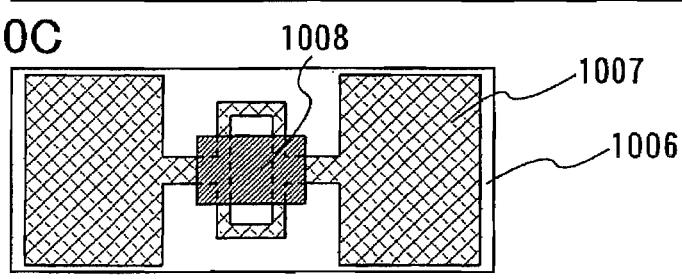

FIG. 10C shows a high frequency antenna. An antenna 1007 is formed over a substrate 1006 and a circuit 1008 using the invention is connected thereto.

Figure 10D:
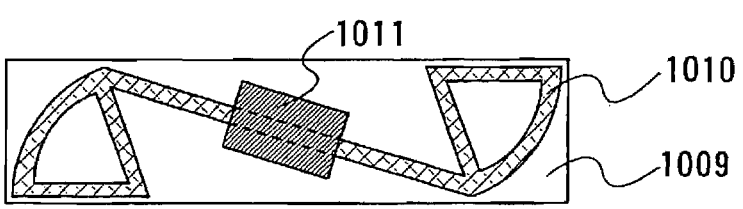

FIG. 10D shows a 180° omnidirectional antenna (capable of receiving signals in any directions). An antenna 1010 is formed over a substrate 1009 and a circuit 1011 using the invention is connected thereto.

Figure 10E:
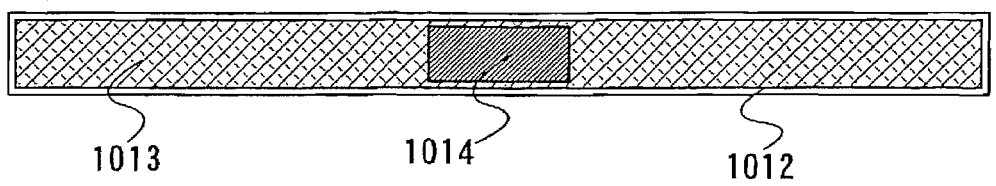

FIG. 10E shows an antenna extended in a stick shape. An antenna 1013 is formed over a substrate 1012 and a circuit 1014 using the invention is connected thereto.

A circuit using the invention and an antenna can be connected by a known method. For example, an antenna and a circuit are connected by wire bonding or bump bonding. Alternatively, a circuit in a chip having an electrode over one surface thereof may be attached to an antenna. In this method, an ACF (Anisotropic Conductive Film) can be used.

An appropriate length required for an antenna varies depending on a frequency for receiving signals. In general, the length is favorably a submultiple of a wavelength. For example in the case where a frequency is 2.45 GHz, the length of antenna may be about 60 mm (½ wavelength) or 30 mm (¼ wavelength).

Figure 11A:
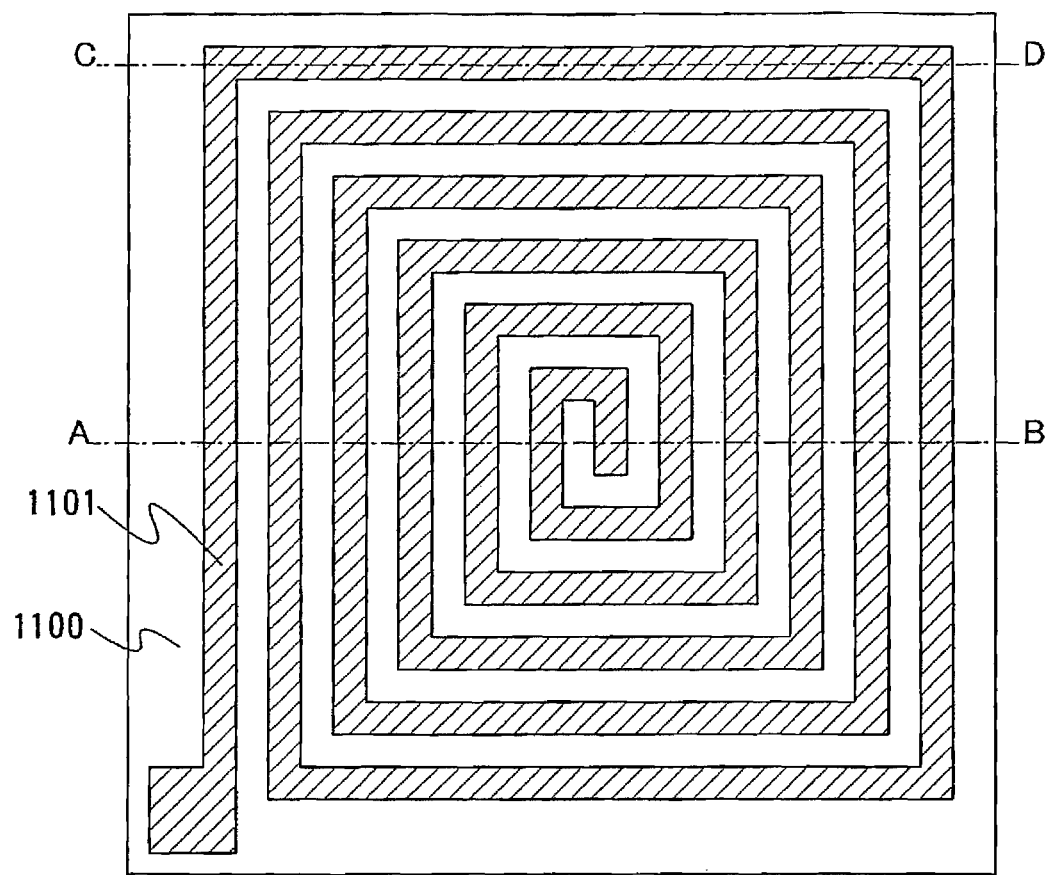
FIGS. 11A to 11C are diagrams showing embodiments of an antenna of the invention.
Figure 11B:
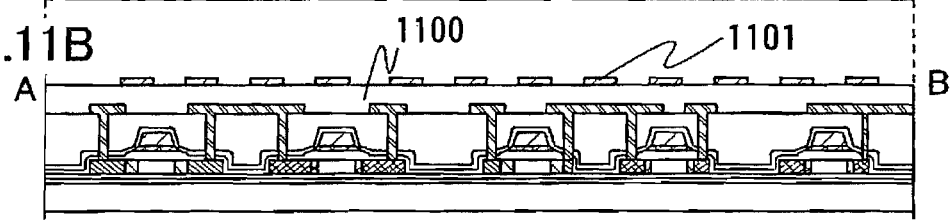
Figure 11C:
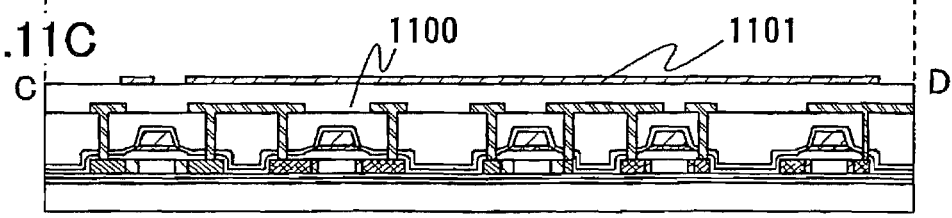

Further, a top substrate 1100 may be mounted over the circuit of the invention and an antenna may be formed thereover. FIGS. 11A to 11C show a top plan view and cross sectional views in which a substrate is mounted over the circuit and an antenna wiring 1101 in a spiral is provided.

The example shown in this embodiment is only an example and does not limit a shape of the antenna. The invention can be implemented with any shape of antenna. This embodiment can be implemented by using any combination of configurations described in the embodiment modes and Embodiments 1 to 6.

[Embodiment 8]

In this embodiment, a specific manufacturing method of a thin film integrated circuit device including a TFT is described with reference to FIGS. 12A to 14B. Here for simplicity, sectional structures of a CPU and a memory portion using an n-type TFT and a p-type TFT are shown to describe a manufacturing method thereof.

Figure 12A:
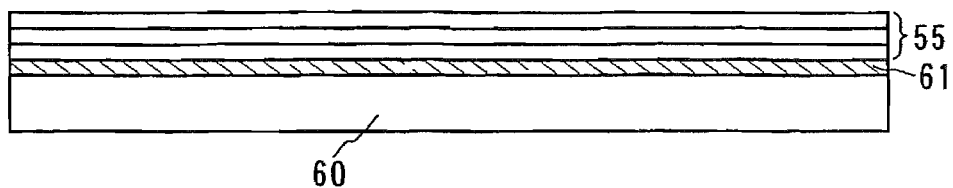
FIGS. 12A to 12E are cross sectional diagrams showing steps of the invention.

First, a peeling layer 61 is formed over a substrate 60 (FIG. 12A). Here, an a-Si film (amorphous silicon film) with a thickness of 50 nm is formed over a glass substrate (for example, Corning 1737 substrate) by low pressure CVD. It is to be noted that a quartz substrate, a substrate formed of an insulating substance such as alumina, a silicon wafer substrate, a plastic substrate having heat resistance against a processing temperature of a subsequent step, and the like as well as a glass substrate can be used as a substrate.

It is preferable that the peeling layer be formed of a film containing silicon as a main component, such as polycrystalline silicon, single crystalline silicon, and SAS (semi-amorphous silicon (also referred to as microcrystalline silicon)) as well as amorphous silicon, however, the invention is not limited to these. The peeling layer may be formed by plasma CVD, sputtering and the like as well as low pressure CVD. Further, a film doped with impurities such as phosphorus may be used as well. The peeling layer preferably has a thickness of 50 to 60 nm. In the case of using SAS, the film thickness may be 30 to 50 nm.

Subsequently, a protective film 55 (also referred to as a base film and a base insulating film) is formed over the peeling layer 61 (FIG. 12A). Here, a three-layer structure of a SiON film with a thickness of 100 nm, a SiNO film with a thickness of 50 nm, and a SiON film with a thickness of 100 nm is employed, however, a material, a thickness, and the number of stacked layers are not limited to these. For example, a heat resistant resin such as siloxane may be formed with a thickness of 0.5 to 3 µm by spin coating, slit coating, a droplet discharge method and the like instead of the SiON film of the bottom layer. Further, a silicon nitride film (SiN, $Si_3N_4$ and the like) may be used as well. Each thickness is preferably 0.05 to 3 µm and can be selected freely in this range.

Here, a silicon oxide film can be formed by thermal CVD, plasma CVD, normal pressure CVD, bias ECRCVD and the like by using a mixed gas of $SiH_4$ and $O_2$, TEOS (tetraethyl orthosilicate) and $O_2$ and the like. Further, a silicon nitride film can be formed by plasma CVD using a mixed gas of $SiH_4$ and $NH_3$. Moreover, the SiON film or SiNO film can be formed by plasma CVD using a mixed gas of $SiH_4$ and $N_2O$.

In the case of using a material containing silicon such as a-Si as a main component for the peeling layer 61 and an island-shaped semiconductor film 57, a protective film to be in contact with them may be formed of $SiO_xN_y$, in view of securing contact.

Subsequently, thin film transistors (TFTs) which form a CPU and a memory of a thin film integrated circuit device are formed over the protective film 55. It is to be noted that a thin film active element such as an organic TFT and a thin film diode can be formed as well as a TFT.

Figure 12B:
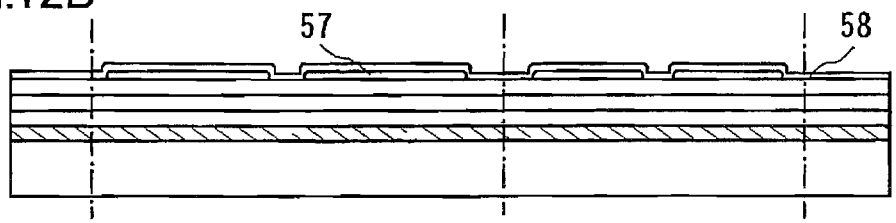

To manufacture a TFT, the island-shaped semiconductor film 57 is formed first over the protective film 55 (FIG. 12B). The island-shaped semiconductor film 57 is formed of an amorphous semiconductor, a crystalline semiconductor, or a semi-amorphous semiconductor. Any of these can be formed by using a semiconductor film containing silicon, silicon germanium (SiGe) and the like as a main component.

Here, an amorphous silicon film is formed with a thickness of 70 nm and a surface thereof is treated with a solution containing nickel. Further, a crystalline silicon semiconductor film is formed by a thermal crystallization step at 500 to 750° C. and laser crystallization is carried out to improve the crystallinity. Moreover, as a deposition method, plasma CVD, sputtering, LPCVD and the like can be used. As a crystallization method, laser crystallization, thermal crystallization, thermal crystallization using other catalyst (Fe, Ru, Rh, Pd, Os, Ir, Pt, Cu, Au and the like) may be performed. Alternatively, these crystallizations may be performed in turn a plurality of times.

As a crystallization process of a semiconductor film having an amorphous structure, a continuous oscillation laser may be used. In order to obtain large grain crystals in crystallization, a second to fourth harmonic of the fundamental wave of a solid state laser capable of oscillating continuously is preferably used (crystallization in this case is referred to as CWLC). Typically, a second (532 nm) and third (355 nm) harmonic of an $Nd:YVO_4$ laser (fundamental wave is 1064 nm) is used. In the case of using a continuous oscillation laser, laser light emitted from a continuous oscillation $YVO_4$ laser with an output of 10 W is converted into a harmonic by a non-linear optical element. Moreover, a harmonic may be emitted by setting a $YVO_4$ crystal or a $GdVO_4$ crystal and a non-linear optical element in a resonator. It is preferable to form into a rectangular or elliptical laser light on an irradiated surface by an optical system for the irradiation on an object. An energy density at this time is required to be about 0.01 to 100 $MW/cm^2$ (preferably 0.1 to 10 $MW/cm^2$). Then, the laser light is irradiated by moving the semiconductor film relatively to laser light at a rate of about 10 to 2000 cm/s.

In the case of using a pulsed oscillation laser, a frequency band of about several tens to several hundreds Hz is typically used, however, a pulsed oscillation laser having a repetition rate of 10 MHz or more, which is drastically higher than the aforementioned band may be used as well (crystallization at this time is referred to as MHzLC). It takes several tens to several hundreds nsec until a semiconductor film irradiated with pulsed oscillation laser light is completely solidified. Therefore, by using the aforementioned high frequency band, next pulse laser can be irradiated until the semiconductor film dissolved by laser light is solidified. Accordingly, a solid-liquid interface of the semiconductor film can be continuously moved, which is different than the case of using a conventional pulsed oscillation laser. Thus, a semiconductor film having crystal grains which are continuously grown in a direction of a scanning direction is formed. In specific, an aggregation of crystal grains of which width in a scanning direction is 10 to 30 μm and the width in a direction perpendicular to the scanning direction is about 1 to 5 μm can be formed. By forming single crystal grains which extend long to the scanning direction, a semiconductor film can be formed in which any crystal grain boundaries hardly exist in at least a channel direction of the TFT.

In the case of using siloxane which is a heat resistant organic resin partially for the protective film 55, it can be prevented that heat leaks from the semiconductor film in crystallization, and thus efficient crystallization can be carried out.

By the aforementioned method, a crystalline silicon semiconductor film is obtained. Note that the crystals are preferably aligned in a source, a channel, and a drain directions. Further, it is preferable that the thickness of the crystalline layer be 20 to 200 nm (typically 40 to 170 nm, or more preferably 50 to 150 nm). After that, an amorphous silicon film for gettering metal catalysts is formed over the semiconductor film with an oxide film interposed therebetween, and then gettering treatment is performed thermally at a temperature of 500 to 750° C. Further, in order to control a threshold value of a TFT element, boron ions are injected at a dosage of about $10^{13}/cm^2$ to a crystalline silicon semiconductor film. After that, the island-shaped semiconductor film 57 is formed by etching with a resist as a mask.

The crystalline semiconductor film can also be formed by directly forming a polycrystalline semiconductor film by LPCVD (Low-Pressure CVD) with disilane ($Si_2H_6$) and germanium fluoride ($GeF_4$) as a source gas. The gas flow rate is $Si_2H_6/GeF_{4=20/0.9}$, a deposition temperature is 400 to 500° C., and He or Ar is used as a carrier gas here, although the invention is not limited to this.

Note that the channel region in particular in a TFT is preferably added hydrogen or halogen of $1\times10^{19}$ to $1\times10^{22}$ $cm^{-3}$ or preferably $1\times10^{19}$ to $5\times10^{20}$ $cm^{-3}$. As for SAS, it is preferable that $1\times10^{19}$ to $2\times10^{21}$ $cm^{-3}$ of hydrogen or halogen be added. In any cases, it is preferable that more hydrogen or halogen be contained than that contained in a single crystal used for an IC chip. Accordingly, even when a crack is generated locally in a TFT portion, hydrogen or halogen can terminate (saturate) it.

Next, a gate insulating film 58 is formed on the island-shaped semiconductor film 57 (see FIG. 12B). It is preferable that the gate insulating film be formed by using a thin film forming method such as plasma CVD or sputtering to form a film containing silicon nitride, silicon oxide, silicon nitride oxide or silicon oxynitride in a single layer or by stacking. In the case of stacking the layers, for example, a three-layer structure is preferably employed in which a silicon oxide film, a silicon nitride film, and a silicon oxide film are stacked in this order from the substrate side.

Figure 12C:
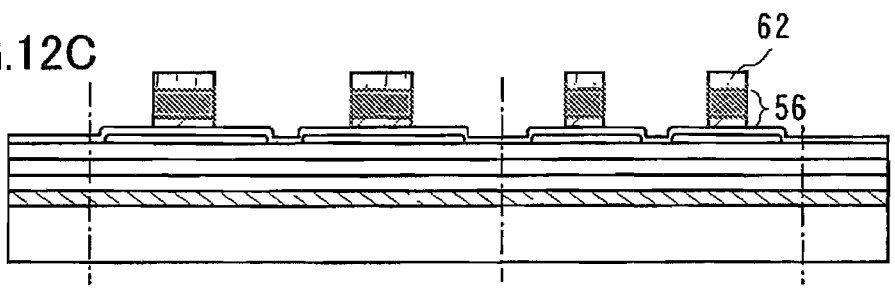
Figure 12D:
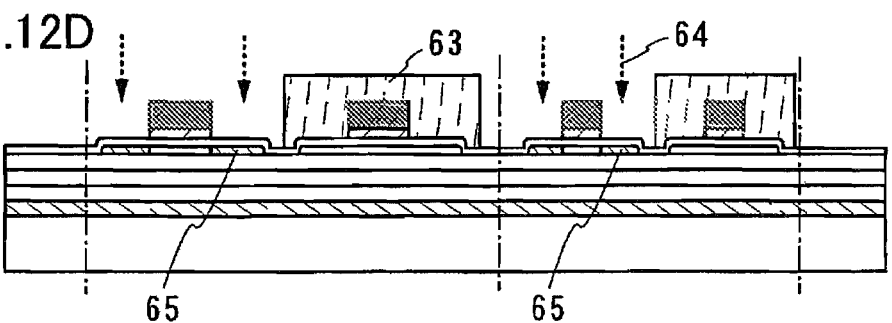

Next, a gate electrode 56 is formed (see FIG. 12C). Here, the gate electrode 56 is formed by stacking Si and W (tungsten) by sputtering and etched with a resist 62 as a mask. It is needless to say that a material, structure, and manufacturing method of the gate electrode 56 are not limited to these and can be appropriately selected. For example, a stacked-layer structure of Si doped with n-type impurities and NiSi (nickel silicide) or a stacked-layer structure of TaN (Tantalum Nitride) and W (tungsten) may be employed as well. Further, a single layer using various conductive materials may be employed.

Further, a mask such as SiOx may be used instead of the resist mask. In this case, a patterning step for forming a mask such as SiOx and SiON (referred to as a hard mask) is additionally required, however, a gate electrode layer having a desired width can be formed as the mask is not decreased as much as the resist in etching. Moreover, the gate electrode 56 may be selectively formed by a droplet discharge method without using the resist 62.

As a conductive material, various materials can be selected according to a function of a conductive film. Further, in the case of forming a gate electrode and an antenna at the same time, a material is to be selected in consideration of functions thereof.

It is to be noted that a mixed gas of $CF_4$, $Cl_2$, and $O_2$ or a $Cl_2$ gas is used as an etching gas for etching the gate electrode, however, the invention is not limited to these.

Subsequently, portions to be p-type TFTs 70 and 72 are covered with a resist 63 and island-shaped semiconductor films in n-type TFTs 69 and 71 are doped with an impurity element 64 which impart n-type conductivity (typically, P (phosphorus) or As (arsenic) is doped at a low concentration (a first doping step, FIG. 12D)) with the gate electrode as a mask. The first doping step is carried out with a condition of a dosage of $1\times10^{13}$ to $6\times10^{13}/cm^2$ and an acceleration voltage of 50 to 70 keV, however, the invention is not limited to this. By the first doping step, through doping is carried out through the gate insulating film 58, thereby a pair of low concentration impurity regions 65 are formed. It is to be noted that the first doping step may be performed to an entire surface without covering the p-type TFT region with a resist.

Figure 12E:
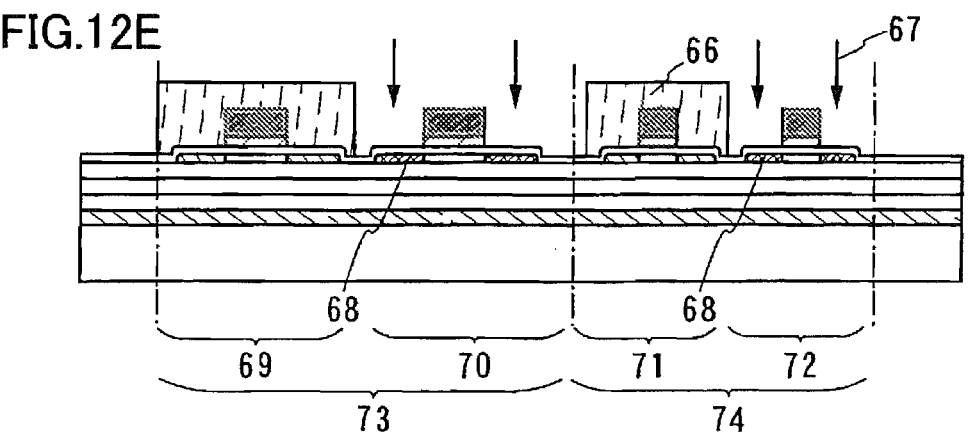

Subsequently, after removing the resist 63 by ashing and the like, a resist 66 to cover the n-type TFT region is additionally formed, and an impurity element 67 (typically boron) which imparts p-type conductivity is doped into the island-shaped semiconductor films of the p-type TFTs 70 and 72 at a high concentration (a second doping step, FIG. 12E). The second doping step is carried out with a condition of a dosage of $1\times10^{16}$ to $3\times10^{16}/cm^2$ and an acceleration voltage of 20 to 40 keV. By this second doping step, through doping is carried out through the gate insulating film 58, thereby a pair of p-type high concentration impurity regions 68 are formed.

Figure 13F:
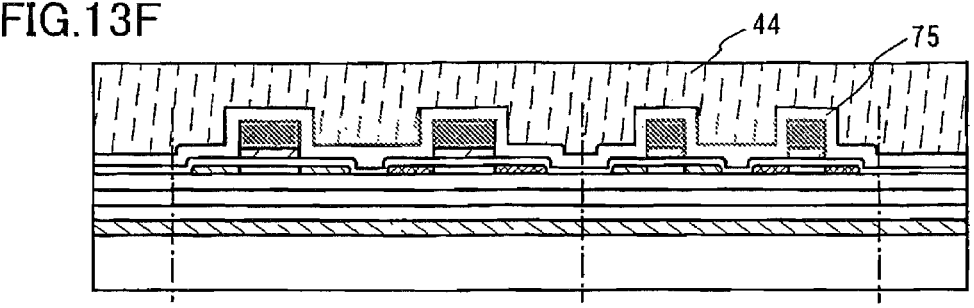
FIGS. 13F to 13I are cross sectional diagrams showing steps of the invention.
Figure 13G:
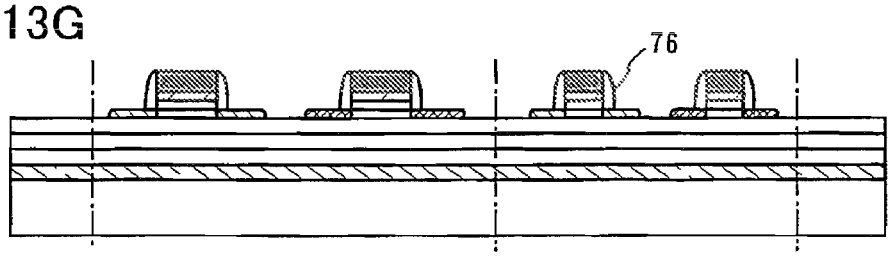

Subsequently, after removing the resist 66 by ashing and the like, an insulating film 75 is formed over the substrate (FIG. 13F). Here, a $SiO_2$ film is formed with a thickness of 100 nm by plasma CVD. After that, the entire substrate is covered with a resist 44 and a side wall 76 is formed in a self-aligned manner by removing the resist 44, the insulating film 75, and the gate insulating film 58 by etching (FIG. 13G). As an etching gas, a mixed gas of $CHF_3$ and He is used. It is to be noted that a step for forming a side wall is not limited to this.

In the case where an insulating film is also formed over a back surface of the substrate when forming the insulating film 75, the insulating film on the back is removed by etching with the resist 44 as a mask (back treatment).

Figure 14A:
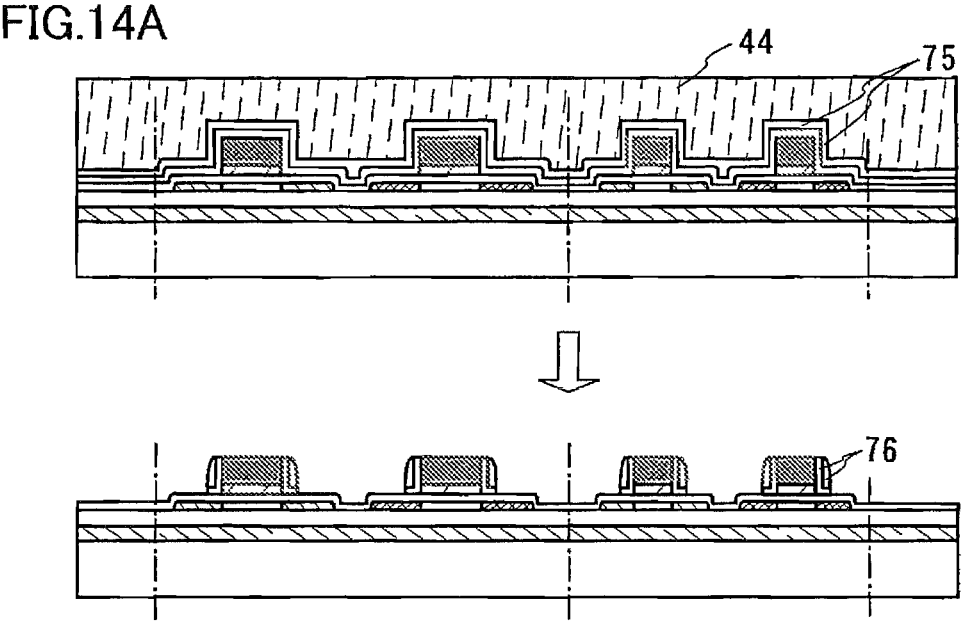
FIGS. 14A and 14B are cross sectional diagrams showing steps of the invention.

It is to be noted that a method for forming the side wall 76 is not limited to the aforementioned. For example, methods shown in FIGS. 14A and 14B can be employed as well. FIG. 14A shows an example where the insulating film 75 has a structure of two or more layers. For example, the insulating film 75 is formed of a SiON (silicon oxynitride) film with a thickness of 100 nm and an LTO (Low Temperature Oxide) film with a thickness of 200 nm. Here, the SiON film is formed by plasma CVD and the LTO film is formed by applying low pressure CVD to a $SiO_2$ film. After that, the side wall 76 having an L shape and a circular shape is formed by applying etch back with the resist 44 as a mask.

Figure 14B:
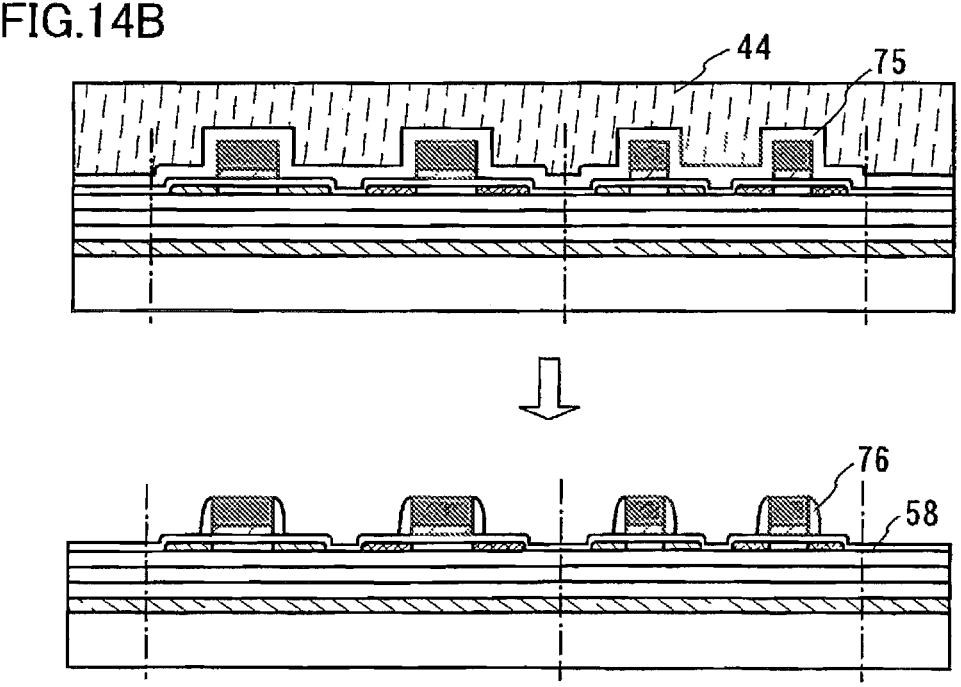

FIG. 14B shows an example where etch back is performed so as to leave the gate insulating film 58. The insulating film 75 in this case may have a single layer structure or a stacked-layer structure.

The sidewall functions as a mask used for doping high concentration of an n-type impurity and forming a low concentration impurity region or a non-doped offset region under the sidewall 76. In any of the aforementioned methods for forming the sidewall, a condition of the etch back may be appropriately changed according to a width of the low concentration impurity region or the offset region to be formed.

Figure 13H:
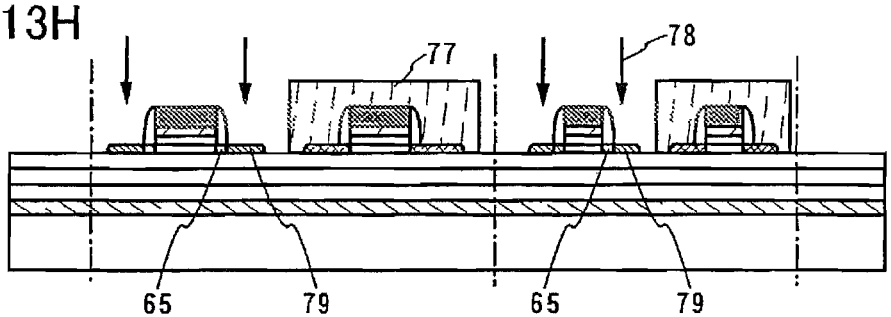

Subsequently, a resist 77 to cover the p-type TFT region is additionally formed and an impurity element 78 (typically P or As) which imparts an n-type conductivity is doped at a high concentration with the gate electrode 56 and the sidewall 76 as masks (a third doping step, FIG. 13H). The third doping step is carried out with a condition of a dosage of $1\times10^{13}$ to $5\times10^{15}/cm^2$ and an acceleration voltage of 60 to 100 keV. By this third doping step, through doping is carried out through the gate insulating film 58, thereby a pair of n-type high concentration impurity regions 79 are formed.

It is to be noted that the impurity region may be thermally activated after removing the resist 77 by ashing and the like. For example, after forming a SiON film with a thickness of 50 nm, thermal treatment may be performed in an nitrogen atmosphere at 550° C. for four hours. Further, by applying thermal treatment in an nitrogen atmosphere at 410°C. for one hour after forming a $SiN_x$ film containing hydrogen with a thickness of 100 nm, a crystal defect of a crystalline semiconductor film can be improved. This treatment is referred to as a hydrogenation step and the like, thereby dangling bonds in crystalline silicon are terminated. Further, as a cap insulating film for protecting TFTs, a SiON film with a thickness of 600 nm is formed. It is to be noted that the hydrogenation step may be performed after forming the SiON film. In this case, a $SiN_x$ film and a SiON film can be continuously deposited. In this manner, an insulating film including three layers of SiON, $SiN_x$, and SiON is formed over the TFT, however, the structure and material are not limited to these. These insulating films are preferably formed as they also have a function to protect TFTs.

Figure 13I:
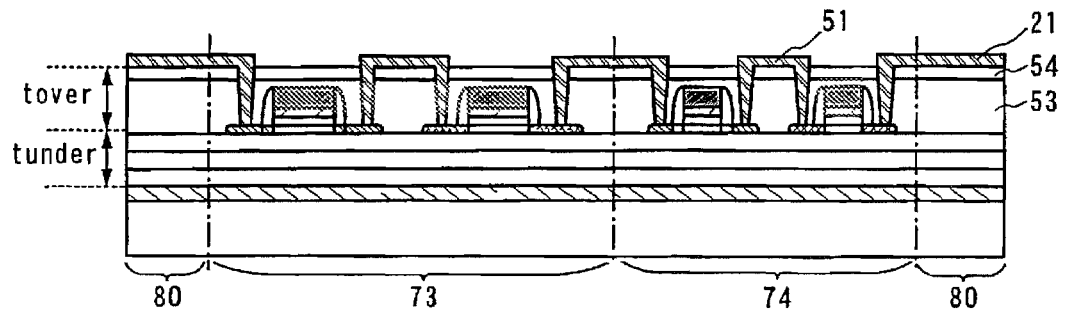

Subsequently, an interlayer film 53 is formed over the TFT (FIG. 13I). The interlayer film 53 can be formed of a heat resistant organic resin such as polyimide, acrylic, polyamide, and siloxane by spin coating, dipping, spray application, a droplet discharge method (ink-jetting, screen printing, offset printing and the like), a doctor knife, a roll coater, a curtain coater, a knife coater and the like. Further, an inorganic material may be used as well, for which silicon oxide, silicon nitride, silicon oxynitride, PSG (phosphorus glass), BPSG (phosphorus boron glass), an alumina film and the like can be used. It is to be noted that these insulating films may be stacked to form the interlayer film 53.

Further, a protective film 54 may be formed over the interlayer film 53. The protective film 54 can be formed of a film containing carbon such as DLC (Diamond-Like Carbon) or carbon nitride (CN), or a silicon oxide film, a silicon nitride film or a silicon nitride oxide film by plasma CVD, atmospheric plasma and the like. Alternatively, a photosensitive or non-photosensitive organic material such as polyimide, acrylic, polyamide, resist or benzocyclobutene, and a heat resistant organic resin such as siloxane may be used.

It is to be noted that a filler may be mixed in the interlayer film 53 or the protective film 54 to prevent that these films are peeled off or cracked due to a stress generated by a difference in a thermal expansion rate between the interlayer film 53 or the protective film 54 and a conductive material or the like which forms a wiring later.

Subsequently, a contact hole is opened by etching after forming a resist, and then a wiring 51 to connect TFTs and a connecting wiring 21 for connecting to an external antenna are formed (FIG. 13I). The contact hole is opened by etching using a mixed gas of $CHF_3$ and He, however, the invention is not limited to this. Further, the wiring 51 and the wiring 21 may be formed of the same material at the same time or separately. Here, the wiring 51 connected to the TFT has a five-layer structure of Ti, TiN, Al—Si, Ti, and TiN, which is formed by sputtering and then patterning.

By mixing silicon in an Al layer, hillock can be prevented from generating in resist baking at a time of patterning. Moreover, about 0.5% of Cu may be mixed instead of Si. Further, by sandwiching an Al—Si layer with Ti and TiN, hillock resistance can be further improved. Note that it is preferable to use the aforementioned hard mask formed of SiON and the like in patterning. Note that the material and the forming method of the wiring are not limited to these, and the material used for the aforementioned gate electrode may be employed as well.

In this embodiment mode, the TFT region including the CPU 73, the memory 74 and the like and a terminal portion 80 connected to an antenna are integrated, however, this embodiment can be applied to the case of integrating the TFT region and the antenna. In this case, it is preferable to form an antenna over the interlayer film 53 or the protective film 54, and then cover the antenna with another protective film. As a conductive material for the antenna, Ag, Au, Al, Cu, Zn, Sn, Ni, Cr, Fe, Co, or Ti, or an alloy containing these can be used, however, the invention is not limited to these. The wiring and antenna may be formed of different materials. It is to be noted that the wiring and antenna are preferably formed to have a highly ductile metal material, and more preferably formed thick enough to resist a stress of deformation.

The wiring and antenna may be formed by patterning using a resist mask after depositing over the entire surface by sputtering or by selectively forming from a nozzle by a droplet discharge method. It is to be noted that the droplet discharge method here is not limited to an ink-jetting but includes offset printing, screen printing and the like. The wiring and antenna may be formed at the same time or one of them may be formed prior to the other so that one overlaps the other.

Through the aforementioned steps, a thin film integrated circuit device formed of TFTs is completed. In this embodiment, a top gate structure is employed, however, a bottom gate structure (inversely staggered structure) may be employed as well. It is to be noted that a base insulating material, an interlayer insulating material, and a wiring material are mainly provided in a region where a thin film active element such as a TFT does not exist. It is preferable that this region occupy 50% or more of the thin film integrated circuit device, and more preferably 70 to 95% thereof. Accordingly, an ID chip can be easily bent and a completed product such as an ID label can be easily handled. In this case, an island-shaped semiconductor region (island) of an active element including a TFT portion preferably occupies 1 to 30% of the thin film integrated circuit device, and more preferably 5 to 15% thereof.

Further, as shown in FIG. 13I, it is preferable to control the thickness of the upper or lower protective film or the interlayer film so that the distance ($t_{under}$) from the semiconductor layer of the TFT to the lower protective film and the distance ($t_{over}$) from the semiconductor layer to the upper interlayer film (the protective layer in the case where the protective layer is formed) are equal or substantially equal to each other in the thin film integrated circuit device. By locating the semiconductor layer in the center of the thin film integrated circuit device in this manner, stress to the semiconductor layer can be eased, and cracks can be prevented.

As described above, the application range of the invention is quite wide and the invention can be applied as a wireless chip which transmits sensed data. Further, the invention can be implemented by using any combination of configurations described in the embodiment modes and Embodiments 1 to 8.

This application is based on Japanese Patent Application serial no. 2004-257646 filed in Japan Patent Office on 3, Sep., 2004, the entire contents of which are hereby incorporated by reference.

What is claimed is:

1. A semiconductor device comprising:
   a circuit comprising a plurality of transistors and an insulating film over and in contact with the plurality of transistors; and
   an antenna over the insulating film,
   wherein the whole of the antenna overlaps the insulating film,
   wherein at least a part of the antenna overlaps at least one of the plurality of transistors, and
   wherein the circuit comprises at least one of a logic circuit, a modulating circuit, and a sensor circuit.

2. The semiconductor device according to claim 1, wherein the sensor circuit is configured to obtain biological information data.

3. The semiconductor device according to claim 1, wherein the circuit further comprises a memory circuit.

4. The semiconductor device according to claim 1, further comprising a battery.

5. The semiconductor device according to claim 1, wherein at least one of the plurality of transistors is a thin film transistor.

6. The semiconductor device according to claim 1, wherein each of the plurality of transistors is a thin film transistor.

7. The semiconductor device according to claim 1, further comprising a substrate.

8. The semiconductor device according to claim 7, wherein the substrate is selected from a silicon substrate, a plastic substrate, a quartz substrate, a glass substrate, and an alumina substrate.

9. The semiconductor device according to claim 7, wherein the substrate has an insulating surface over which the circuit is located.

10. The semiconductor device according to claim 7, wherein the substrate is a flexible substrate.

11. The semiconductor device according to claim 7,
    wherein each of the plurality of transistors is formed over a second insulating film which is located over the substrate, and
    wherein a thickness of the second insulating film and a thickness of the insulating film are equal or substantially equal to each other.

12. A data collecting system comprising the semiconductor device according to claim 1.

13. A semiconductor device comprising:
    a circuit comprising a plurality of transistors and an insulating film over and in contact with the plurality of transistors; and
    an antenna over the insulating film,
    wherein the whole of the antenna overlaps the insulating film,
    wherein at least a part of the antenna overlaps at least one of the plurality of transistors, and
    wherein the antenna has a coil shape.

14. The semiconductor device according to claim 13, wherein the circuit further comprises a memory circuit.

15. The semiconductor device according to claim 13, further comprising a battery.

16. The semiconductor device according to claim 13, wherein at least one of the plurality of transistors is a thin film transistor.

17. The semiconductor device according to claim 13, wherein each of the plurality of transistors is a thin film transistor.

18. The semiconductor device according to claim 13, further comprising a substrate.

19. The semiconductor device according to claim 18, wherein the substrate is selected from a silicon substrate, a plastic substrate, a quartz substrate, a glass substrate, and an alumina substrate.

20. The semiconductor device according to claim 18, wherein the substrate has an insulating surface over which the circuit is located.

21. The semiconductor device according to claim 18, wherein the substrate is a flexible substrate.

22. The semiconductor device according to claim 18,
    wherein each of the plurality of transistors is formed over a second insulating film which is located over the substrate, and
    wherein a thickness of the second insulating film and a thickness of the insulating film are equal or substantially equal to each other.

23. A data collecting system comprising the semiconductor device according to claim 13.

* * * * *